(12) United States Patent
Miura et al.

(10) Patent No.: US 10,706,965 B2
(45) Date of Patent: Jul. 7, 2020

(54) SENSOR INFORMATION ACQUIRING DEVICE, SENSOR INFORMATION ACQUIRING METHOD, RECORDING MEDIUM IN WHICH SENSOR INFORMATION ACQUIRING PROGRAM IS RECORDED, AND MEDICAL INSTRUMENT

(71) Applicant: Olympus Corporation, Hachioji-shi, Tokyo (JP)

(72) Inventors: Hiroaki Miura, Hachioji (JP); Kenta Yumoto, Hachioji (JP); Ko Kimura, Akiruno (JP); Osamu Nonaka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 38 days.

(21) Appl. No.: 15/853,706

(22) Filed: Dec. 22, 2017

(65) Prior Publication Data
US 2018/0182486 A1 Jun. 28, 2018

(30) Foreign Application Priority Data
Dec. 26, 2016 (JP) ................. 2016-251717

(51) Int. Cl.
*G06K 9/00* (2006.01)
*G16H 40/63* (2018.01)
(Continued)

(52) U.S. Cl.
CPC ............ *G16H 40/63* (2018.01); *G06F 1/163* (2013.01); *G06F 1/1686* (2013.01); *G06F 3/011* (2013.01); *G06F 3/012* (2013.01); *G06F 3/014* (2013.01); *G06F 3/017* (2013.01); *G06F 3/0488* (2013.01); *G06T 7/0012* (2013.01); *G06T 7/246* (2017.01);
(Continued)

(58) Field of Classification Search
CPC .............. G06F 1/163; G06F 1/1686; G06F 2200/1637; G06F 3/011; G06F 3/012; G06F 3/01488; G06T 2207/10068; G06T 2207/20104; G06T 7/0012; G06T 7/246; G16H 30/40; G16H 40/63; H04N 5/2251; H04N 5/2253; H04N 5/2259;
(Continued)

(56) References Cited

U.S. PATENT DOCUMENTS 8,761,412 B2 * 6/2014 Hernandez-Abrego ..................... H04R 3/005 381/92
9,274,597 B1 * 3/2016 Karakotsios .......... G06F 3/0346
(Continued)

FOREIGN PATENT DOCUMENTS

JP 2007-222239 9/2007

*Primary Examiner* — Ian L Lemieux
(74) *Attorney, Agent, or Firm* — John C. Pokotylo; Pokotylo Patent Services

(57) ABSTRACT

A sensor information acquiring device includes a sensor and a control section configured to determine that a position of a target object does not change even if a relative relation between the sensor and the target object changes and control an information acquisition direction of the sensor on the basis of information concerning displacement of a displacement section to which the sensor is attached. Even when a position, a direction, and the like of the sensor are changed by influence of work and the like, the sensor information acquiring device can always acquire effective sensor information concerning a desired target object.

20 Claims, 12 Drawing Sheets

(51) Int. Cl.

| | |
|---|---|
| *G06T 7/00* | (2017.01) |
| *G16H 30/40* | (2018.01) |
| *G06F 3/0488* | (2013.01) |
| *H04N 5/225* | (2006.01) |
| *H04R 29/00* | (2006.01) |
| *G06F 3/01* | (2006.01) |
| *H04N 5/262* | (2006.01) |
| *H04R 3/00* | (2006.01) |
| *H04R 1/02* | (2006.01) |
| *G06F 1/16* | (2006.01) |
| *G06T 7/246* | (2017.01) |
| *H04R 1/40* | (2006.01) |
| *G16H 20/40* | (2018.01) |

(52) U.S. Cl.
CPC ........... *G16H 30/40* (2018.01); *H04N 5/2251* (2013.01); *H04N 5/2253* (2013.01); *H04N 5/2259* (2013.01); *H04N 5/2628* (2013.01); *H04R 1/028* (2013.01); *H04R 3/005* (2013.01); *H04R 29/004* (2013.01); *G06T 2207/10068* (2013.01); *G06T 2207/20104* (2013.01); *G16H 20/40* (2018.01); *H04R 1/406* (2013.01)

(58) Field of Classification Search
CPC ...... H04N 5/2628; H04R 1/028; H04R 1/406; H04R 29/004; H04R 3/005
See application file for complete search history.

(56) References Cited

U.S. PATENT DOCUMENTS

| | | | |
|---|---|---|---|
| 2013/0326364 A1* | 12/2013 | Latta | G06F 3/012 715/751 |
| 2014/0222462 A1* | 8/2014 | Shakil | G06Q 50/22 705/3 |
| 2016/0063727 A1* | 3/2016 | Gao | G06K 9/00335 382/103 |
| 2016/0161589 A1* | 6/2016 | Benattar | G01S 3/803 367/129 |
| 2016/0225192 A1* | 8/2016 | Jones | G06F 3/012 |
| 2016/0232879 A1* | 8/2016 | Han | G06F 3/04842 |
| 2016/0249989 A1* | 9/2016 | Devam | A61B 5/024 345/633 |
| 2016/0324598 A1* | 11/2016 | Bothorel | A61B 90/50 |
| 2017/0307891 A1* | 10/2017 | Bucknor | G06F 3/012 |
| 2017/0336862 A1* | 11/2017 | Xu | G06F 3/038 |
| 2018/0108179 A1* | 4/2018 | Tomlin | G06T 19/006 |
| 2019/0215636 A1* | 7/2019 | Norris | G06K 9/00228 |

* cited by examiner

SENSOR INFORMATION ACQUIRING DEVICE, SENSOR INFORMATION ACQUIRING METHOD, RECORDING MEDIUM IN WHICH SENSOR INFORMATION ACQUIRING PROGRAM IS RECORDED, AND MEDICAL INSTRUMENT

CROSS REFERENCE TO RELATED APPLICATION

This application claim is benefit of Japanese Application No. 2016-251717 in Japan on Dec. 26, 2016, the contents of which are incorporated by this reference.

BACKGROUND OF THE INVENTION

1. Field of the Invention

The present invention relates to a sensor information acquiring device, a sensor information acquiring method, a recording medium in which a sensor information acquiring program is recorded, and a medical instrument for acquiring sensor information of a sensor, a position and a direction of which change, for example, a sensor mounted on a wearable device.

2. Description of the Related Art

A photographing device and a recording device acquire information such as image information and sound information (hereinafter referred to as sensor information) with an image sensor and a sensor of a microphone or the like. A sensor can sometimes acquire more useful information when a disposition position and a disposition direction of the sensor are changed because of limitation of a range in which the sensor information is acquired. A device has also been developed that can change an effective acquisition range of sensor information without changing a disposition position and a disposition direction of a sensor.

For example, a microphone device has also been developed that has a directivity switching function capable of switching, by using a plurality of microphones, a direction in which high sensitivity is obtained. For example, a user switches directivity and designates in which direction sensitivity is increased. Consequently, the user is capable of increasing sensitivity in a desired direction without changing the directions of the microphones.

In the image sensor, when an angle of view is determined by a focal length of an optical lens, which makes an object optical image incident on an image pickup surface of the image sensor, and a size of the image pickup surface and an optical axis direction of the optical lens and an object distance are determined, a photographing range is determined. The user can change the photographing range by changing a direction of a photographing device. Besides, the angle of view can be changed by, for example, a zoom function or switching of an image pickup area. Japanese Patent Application Laid-Open Publication No. 2007-222239 proposes an intra-body cavity observation device that, during a medical practice by a laparoscope device, detects a position of a distal end portion of a treatment instrument located in a body cavity and tracks the distal end portion of the treatment instrument such that the distal end portion is located in a center of an image of a monitor.

In this way, the microphone having the directivity for increasing sensitivity in the direction designated by the user and the photographing device that sets, as the photographing center, the direction designated by the user have been developed. Consequently, it is possible to acquire sensor information concerning a desired target object without changing a disposition position and a disposition direction of the microphone or the photographing device depending on the user.

SUMMARY OF THE INVENTION

A sensor information acquiring device according to an aspect of the present invention includes: a sensor; and a control section configured to determine that a position of a target object does not change even if a relative relation between the sensor and the target object changes and control an information acquisition direction of the sensor on the basis of information concerning displacement of a displacement section to which the sensor is attached.

A sensor information acquiring method according to an aspect of the present invention includes: determining that a position of a target object does not change even if a relative relation between a sensor and the target object changes; acquiring information concerning displacement of a displacement section to which the sensor is attached; and controlling an information acquisition direction of the sensor on the basis of the acquired information concerning the displacement.

A recording medium in which a sensor information acquiring program is recorded according to an aspect of the present invention records the sensor information acquiring program for causing a computer to execute: a procedure for determining that a position of a target object does not change even if a relative relation between a sensor and the target object changes; a procedure for acquiring information concerning displacement of a displacement section to which the sensor is attached; and a procedure for controlling an information acquisition direction of the sensor on the basis of the acquired information concerning the displacement.

A medical instrument according to an aspect of the present invention includes: a displaceable treatment section; a sensor, a positional relation of which with the treatment section is fixed; an information acquiring section configured to determine that a position of a target object does not change even if a relative relation between the sensor and the target object changes and acquire information concerning displacement of the treatment section; and a control section configured to control an information acquisition direction of the sensor on the basis of the acquired information concerning the displacement.

The above and other objects, features and advantages of the invention will become more clearly understood from the following description referring to the accompanying drawings.

DETAILED DESCRIPTION OF THE PREFERRED EMBODIMENTS

Embodiments of the present invention are explained in detail below with reference to the drawings.

First Embodiment

Figure 1:
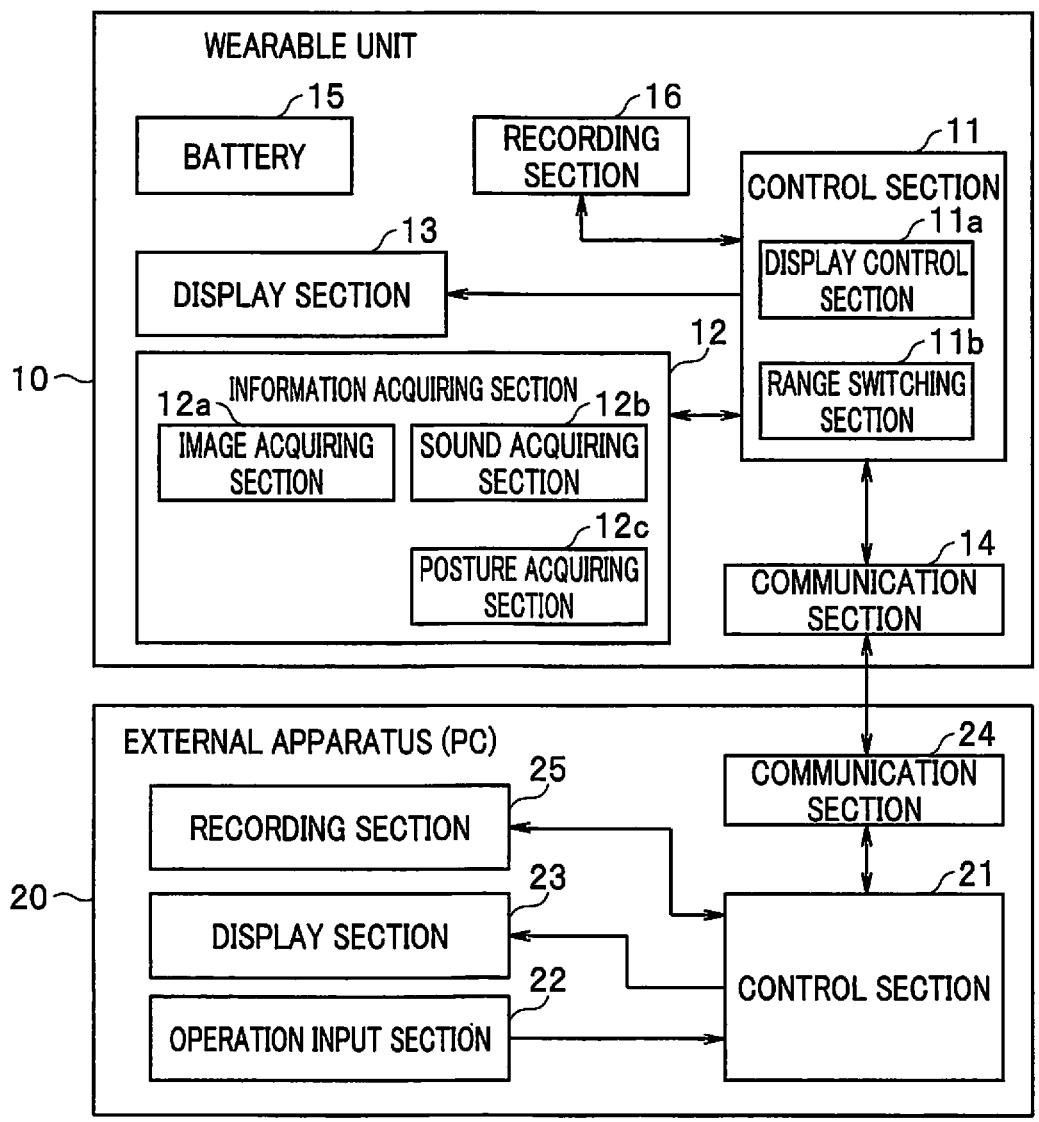
FIG. 1 is a block diagram showing a sensor information acquiring device according to a first embodiment of the present invention.

FIG. 1 is a block diagram showing a sensor information acquiring device according to a first embodiment of the present invention. FIG. 1 shows an example in which an information processing system is configured by an external apparatus 20 and a wearable unit 10 configuring the sensor information acquiring device. In the present embodiment, the external apparatus 20 is not a component essential for the sensor information acquiring device.

In the present embodiment, a target object (hereinafter referred to as tracking target object as well), which is a generation source of sound information acquired by a microphone, is set, a change in a direction from the microphone to the tracking target object is detected by a predetermined sensor on the basis of a direction of the microphone at a time of the setting, and directivity of the microphone is controlled according to a change in a relative positional relation between the microphone and the tracking target object to make it possible to always acquire effective sound information from the tracking target object. The positional relation between the microphone and the target object changes according to a movement on the microphone side and according to a movement on the target object side. The application attempts to take measures against a change in the relative positional relation caused by a posture, behavior, and the like of a user that occur because the microphone or the like is a wearable device.

Consequently, even when the direction of the microphone is changed as a result of the user performing some work or the like, it is always possible to perform directivity control for increasing sensitivity in a tracking target object direction and efficiently collect a sound from the tracking target object direction. It is assumed that a movement of the target object is relatively small. Therefore, it is predominantly described that device performance is corrected solely with respect to a movement of a body of the user. However, when the target object changes, a state of the change may be monitored to change control according to a result of the monitoring. In a situation in which it is possible to grasp a relation between a background and the target object and the relation does not greatly change, a target of compensation of a movement is considered to be a movement of the user. The movement of the user has a characteristic and a limitation in a way of the movement according to a wearing part. Therefore, movement compensation control for controlling directivity of the microphone assuming a movement peculiar to the part may be performed.

The application mainly overcomes a problem caused because, although the target object has a relatively small movement, an instrument or a device worn on the body of the user changes a direction because of behavior of the user, work, or the like while the user is unaware of the change. The eyeglass-type terminal also changes a direction according to a movement of a face of the user. A wristwatch-type terminal frequently changes a direction according to a movement of a hand. If the user concentrates on work or the like, the user has little time to pay attention to a change in a state of the instrument or the device. However, even in such a situation, it is important to continue to assist the user. It is also assumed that a position change of the target object is relatively small compared with influence due to a movement of the body of the user. However, this is not always an essential condition.

The wearable unit 10 includes a not-shown locking section configured to attach a housing incorporating a circuit shown in FIG. 1 to a part of the body of the user. The wearable unit 10 is displaceable according to a movement of the user. For example, when the wearable unit 10 is configured as an eyeglass type, temples of eyeglasses function as the locking section. The entire wearable unit 10 moves according to the movement of the face of the user.

The wearable unit 10 includes a control section 11. The control section 11 controls respective sections of the wearable unit 10. The control section 11 may be configured by a processor in which a CPU or the like is used. The control section 11 may operate according to a computer program stored in a not-shown memory to control the respective sections. A part of the control section 11 may be replaced with a hardware electronic circuit.

A display control section 11a is provided in the control section 11. The display control section 11a executes various kinds of processing concerning display. The display control section 11a can be configured by, for example, a video controller or a display controller. The display control section 11a may be configured separately from the control section 11. The display control section 11a controls display of a display section 13. The display section 13 includes a display screen such as an LCD and displays an image given from the display control section 11a. For example, the display control section 11a can display a picked-up image outputted from an image acquiring section 12a explained below on the display screen of the display section 13.

The wearable unit 10 includes an information acquiring section 12. The information acquiring section 12 acquires sensor information concerning a tracking target object, acquisition of information of which is desired by the user. The information acquiring section 12 includes, for example, an image acquiring section 12a, a sound acquiring section 12b, and a posture acquiring section 12c. The image acquiring section 12a can be configured by, for example, a not-shown image sensor. The image acquiring section 12a can pick up an image of the tracking target object and acquire a picked-up image. The image acquiring section 12a is configured to output the acquired picked-up image to the control section 11 as sensor information. In the present embodiment, a wide-angle lens is adopted by the image acquiring section 12a. Therefore, the image acquiring section 12a is configured to be capable of acquiring a wide-angle image.

The sound acquiring section 12b can be configured by, for example, a microphone. The sound acquiring section 12b can acquire a sound from the tracking target object. In the present embodiment, the sound acquiring section 12b is configured to be capable of controlling directivity. The sound acquiring section 12b is controlled by the control section 11 to a direction in which sensitivity is highest (hereinafter referred to as beam direction). That is, the beam direction is an information acquisition direction by the sound acquiring section 12b. For example, the sound acquiring section 12b can be configured by a microphone device, an orientation of which is variable.

The microphone device, the orientation of which is variable, may be configured by, for example, a plurality of omnidirectional microphones arrayed in a predetermined direction. For example, two omnidirectional microphones having equal characteristics are disposed at a predetermined interval. A sound signal arrives at the microphones from a predetermined direction θ. The sound signal arrives at the respective microphones at different propagation delay time periods according to route differences of the sound signal with respect to the respective microphones. A difference between the propagation delay time periods can be calculated according to the interval between the microphones and the arriving direction θ. By delaying, with a delay circuit having a variable delay amount, an output of one microphone, at which the sound signal arrives earlier, by a delay amount equivalent to the difference between the propagation delay time periods, it is possible to match a phase of the output of the one microphone with a phase of an output of the other microphone, at which the sound signal arrives later. Therefore, it is possible to obtain a largest output with respect to the arriving direction θ by adding up an output of the delay circuit and the output of the other microphone. Note that a phase of the output of the delay circuit with respect to the sound signal from a direction other than the arriving direction θ does not coincide with the phase of the output of the other microphone. An addition result is not the largest output. That is, in this case, in the device, the arriving direction θ is the beam direction. By setting the delay amount of the delay circuit as appropriate, it is possible to obtain a variable directivity microphone device in which any direction is the beam direction. When such a variable directivity microphone device is adopted as the sound acquiring section 12b, the control section 11 is capable of setting the beam direction, that is, an information acquisition direction to a desired direction by setting, in the delay circuit, a delay amount corresponding to a beam direction desired to be designated.

In the present embodiment, the information acquiring section 12 is also used to acquire information in the tracking target object direction for determining the beam direction of the sound acquiring section 12b. The image acquiring section 12a is configured to acquire a wide-angle image having a sufficiently wide angle of view. Even when a field-of-view range of the image acquiring section 12a changes because the user changes, for example, a direction of the face, it is highly likely that the image acquiring section 12a continues to pick up an image of a part of an image pickup range before the field-of-view range change. The picked-up image by the image acquiring section 12a is given to a range switching section 11b of the control section 11. Picked-up images before and after the field-of-view range change are given to the range switching section 11b from the image acquiring section 12a. When the user changes a direction, it is possible to detect an angle of the change with an image analysis of the picked-up images.

For example, the range switching section 11b may be configured to automatically set a tracking target object with the image analysis. For example, when detecting with the image analysis that an image portion of a face and a mouth of a person is present in a center of a picked-up image given from the image acquiring section 12a, the range switching section 11b may set the face and the mouth as the tracking target object. For example, the range switching section 11b may be configured to receive designation operation of the tracking target object by the user and perform setting of a target section. For example, in a state in which a picked-up image acquired by the image acquiring section 12a is displayed on the display screen of the display section 13, the range switching section 11b may cause a not-shown operation section to display a pointer on the image. When a portion on the image is designated by the user with the pointer, the range switching section 11b may set the image portion as the tracking target object. For example, when detecting designation operation for the person on the image, the range switching section 11b may calculate feature values of respective portions of the image with the image analysis of the picked-up image, determine that the respective image portions are the face and the mouth of the person referring to a database of feature values of respective images stored in a not-shown memory, and set the image portions of the face and the mouth of the person as the tracking target object.

The range switching section 11b calculates, with the image analysis, a position on the image of the track target object before the field-of-view range change and a position on the image of the track target object after the field-of-view range change and calculates a difference between view angles that gives a difference between the positions. The range switching section 11b is configured to generate a control signal for changing the beam direction by the calculated difference between the view angles and output the control signal to the sound acquiring section 12b. For example, the range switching section 11b generates, as the control signal, a control signal for setting the delay amount of the delay circuit of the variable directivity microphone device explained above.

Note that, for example, when a generation source of a sound is only one person, the range switching section 11b may determine, as a direction of the tracking target object, a direction in which a largest sound output level is obtained. In this case, information concerning the tracking target object direction can also be acquired by the sound acquiring section 12b. The sound acquiring section 12b is controlled by the range switching section 11b to be capable of changing the beam direction. The range switching section 11b may monitor a sound output level while sweeping the beam direction to determine, as a sound arriving direction, that is, the tracking target object direction, a direction in which a highest sound output level is obtained.

In the present embodiment, the determination of the direction of the tracking target object can also be performed by the posture acquiring section 12c. The posture acquiring section 12c is configured to be capable of determining a posture of the wearable unit 10 and outputting a determination result to the range switching section 11b. For example, the posture acquiring section 12c can be configured by an acceleration sensor, a gyro sensor, a terrestrial magnetism sensor, and the like. The posture acquiring section 12c can determine a posture of the wearable unit 10 on the basis of determination results of the sensors. The explanation is based on the premise that a posture (behavior, etc.) of the user is a main factor of a relative position change with respect to the target object. Therefore, in order to guarantee the premise, the posture acquiring section 12c may first confirm a result obtained by determining in an image given from the image acquiring section that the target object is present in the same position in a background. This may be determined in a situation in which the device is used. A dedicated device may be designed on the premise that a position of the target object is substantially the same.

The range switching section 11b is given a determination result of the posture before the field-of-view range change and a determination result of the posture after the field-of-view range change from the posture acquiring section 12c. The range switching section 11b can calculate, on the basis of a change of the determination results of the postures, a change in an angle in the tracking target object direction that changes according to the change of the postures. The range switching section 11b is configured to generate a control signal for returning the beam direction to an original direction by the calculated change in the angle and output the control signal to the sound acquiring section 12b.

A communication section 14 is provided in the wearable unit 10. The communication section 14 is controlled by the control section 11 to be capable of performing communication by wire or radio between the communication section 14 and the external apparatus 20. For example, the communication section 14 can be configured by various controllers corresponding to a transmission line between the communication section 14 and the external apparatus 20. For example, a LAN controller is adopted as the communication section 14 when a LAN cable is adopted as the transmission line. A wireless LAN controller is adopted as the communication section 14 when Wi-Fi is adopted as the transmission line. A USB controller is adopted as the communication section 14 when the transmission line is a USB cable. A video controller is adopted as the communication section 14 when the transmission line is a video cable.

The control section 11 is configured to be capable of controlling the communication section 14 to transmit the picked-up image given from the image acquiring section 12a to the external apparatus 20. The control section 11 can control the communication section 14 to receive information from the external apparatus 20.

A recording section 16 is provided in the wearable unit 10. The recording section 16 is controlled by the control section 11 to be capable of recording an image and a sound acquired in the information acquiring section 12 in a not-shown recording medium such as a memory. The recording section 16 is configured to be capable of reading out and reproducing the image and the sound recorded in the not-shown recording medium and outputting the reproduced image and the reproduced sound to the control section 11. Consequently, the control section 11 is capable of causing, for example, the display section 13 to display the image recorded by the recording section 16.

A battery 15 is incorporated in the wearable unit 10. The battery 15 is controlled by the control section 11 to generate electric power supplied to the respective sections of the wearable unit 10.

In the present embodiment, for example, a personal computer can be adopted as the external apparatus 20. The external apparatus 20 includes a control section 21. The control section 21 controls respective sections of the external apparatus 20. The control section 21 may be configured by a processor in which a CPU or the like is used. The control section 21 may operate according to a computer program stored in a not-shown memory to control the respective sections. A part of the control section 21 may be replaced with a hardware electronic circuit.

A display section 23 is provided in the external apparatus 20. The control section 21 controls display of the display section 23. The display section 23 includes a display screen such as an LCD and displays an image given from the control section 21. An operation input section 22 is provided in the external apparatus 20. The operation input section 22 includes a not-shown input device such as a keyboard. The operation input section 22 is configured to generate an operation signal based on user operation and supply the operation signal to the control section 21. Consequently, the control section 21 is configured to be capable of executing processing corresponding to the user operation.

A not-shown touch panel may be provided on the display screen of the display section 23. The touch panel can generate an operation signal corresponding to a position on the display screen pointed by the user with a finger. The operation signal is supplied to the control section 21. Consequently, when the user touches the display screen or slides a finger on the display screen, the control section 21 can detect the operation. That is, the control section 21 is configured to be capable of detecting a touch position of the user, operation for closing and opening fingers (pinch operation), slide operation and a position reached by the slide operation, a slide direction, a touching period, and the like and executing processing corresponding to the user operation.

In the above explanation, an example is explained in which the range switching section 11b performs the setting processing for the tracking target object. However, the control section 21 of the external apparatus 20 may cooperate with the range switching section 11b to perform the setting processing for the tracking target object. For example, in a state in which the picked-up image acquired by the image acquiring section 12a is displayed on the display screen of the display section 23, when a portion on the image is designated by touch panel operation of the user, the control section 21 may set the image portion as the tracking target object. For example, when detecting touch operation on a person on the image, the control section 21 may calculate feature values of respective portions of the image with an image analysis of the picked-up image, determine that the respective image portions are a face and a mouth of the person referring to a database of feature values of respective images stored in a not-shown memory, and set the image portion of the face and the mouth of the person as the tracking target object. In this case, the control section 21 transmits information concerning the tracking target object to the range switching section 11b via a communication section 24 and the communication section 14.

A recording section 25 is provided in the external apparatus 20. The recording section 25 is controlled by the control section 21 to be capable of recording an image and a sound in a not-shown recording medium such as a hard disk, a memory, or a disk medium. The recording section 25 is configured to be capable of reading out and reproducing the image and the sound recorded in the not-shown recording medium and outputting the reproduced image and the reproduced sound to the control section 21. Consequently, the control section 21 is capable of, for example, causing the display section 23 to display the image recorded by the recording section 25.

The communication section 24 is provided in the external apparatus 20. The communication section 24 is controlled by the control section 21 to be capable of performing communication by wire or radio between the communication section 24 and the wearable unit 10. For example, the communication section 24 can be configured by various controllers corresponding to a transmission line between the communication section 24 and the wearable unit 10. For example, a LAN controller is adopted as the communication section 24 when a LAN cable is adopted as the transmission line. A wireless LAN controller is adopted as the communication section 24 when Wi-Fi is adopted as the transmission line. A USB controller is adopted as the communication section 24 when the transmission line is a USB cable. A video controller is adopted as the communication section 24 when the transmission line is a video cable.

The control section 21 is configured to be capable of giving, when a picked-up image given from the image acquiring section 12a of the wearable unit 10 is transmitted via the communication sections 14 and 24, the picked-up image to the display section 23 and causing the display section 23 to display the picked-up image on the display screen of the display section 23. For example, the control section 21 is also capable of enlarging a part of the picked-up image acquired in the image acquiring section 12a and causing the display section 23 to display the part of the picked-up image.

Figure 2:
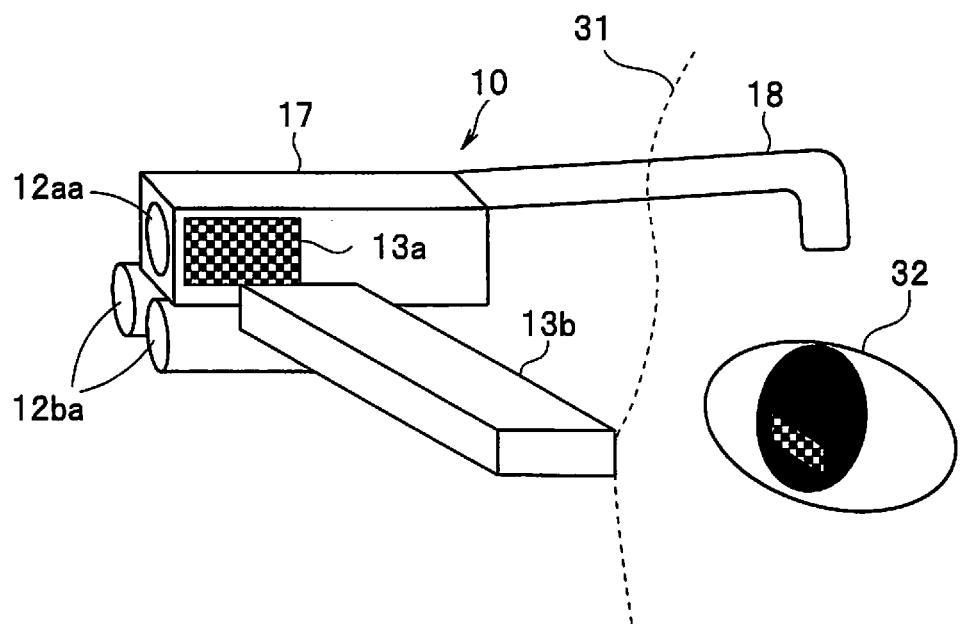
FIG. 2 is an explanatory diagram for explaining an exterior of a wearable unit 10 in FIG. 1.
Figure 3:
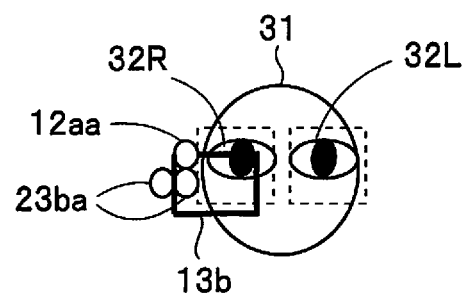
FIG. 3 is an explanatory diagram showing a positional relation between respective sections of the wearable unit 10 and a face.

FIG. 2 is an explanatory diagram for explaining an exterior of the wearable unit 10 in FIG. 1. FIG. 2 shows an example in which the wearable unit 10 is configured by an eyeglass-type wearable terminal device (an eyeglass-type terminal device). FIG. 3 is an explanatory diagram showing a positional relation between the respective sections of the wearable unit 10 and a face.

In FIG. 2, a circuit housing section 17, in which respective circuits configuring a part of the control section 11, the information acquiring section 12, the display section 13, and the communication section 14 in FIG. 1 are housed, is disposed in a part of an eyeglass frame 18. An image pickup lens 12aa configuring the image acquiring section 12a is disposed at a distal end of the circuit housing section 17 to be capable of observing a state of operation. An optical image from an object is given to, via the image pickup lens 12aa, an image pickup device of the image acquiring section 12a provided in the circuit housing section 17. A picked-up image based on an object optical image can be acquired by the image pickup device. In the example shown in FIG. 2, the image pickup lens 12aa is provided at a distal end of a temple portion of the eyeglass frame 18. The temple portion faces substantially the same direction as a direction that a face 31 of a person faces. Therefore, the image acquiring section 12a is capable of picking up an image of the object in the same direction as an observation direction by an eye 32 of the person. Consequently, the image acquiring section 12a is capable of acquiring, as a picked-up image, an image corresponding to a work state observed by the person. As explained above, the control of the beam direction in the sound acquiring section 12b is performed on the basis of the picked-up image acquired by the image acquiring section 12a.

Two microphones 12ba configuring the sound acquiring section 12b are disposed below the image pickup lens 12aa. In the sound acquiring section 12b disposed in the wearable unit 10, the two microphones 12ba are fixed to the eyeglass frame 18. A direction in which the microphones 12ba are directed changes according to a direction of the eyeglass frame 18, that is, a direction of the wearable unit 10 mounted on the face by the eyeglass frame 18. The beam direction can be controlled to a predetermined direction by the range switching section 11b irrespective of the direction in which the microphones 12ba are directed.

A light guide section 13b supported by the eyeglass frame 18 is provided on a front side of a right lens of left and right lenses fit in not-shown left and right rims. A display panel 13a configured to emit video light toward an incident surface of the light guide section 13b is disposed on a side surface of the circuit housing section 17. An emission surface of the light guide section 13b is disposed in a position corresponding to a part of a region of the right lens in front of the right eye 32 in a state in which the eyeglass frame 18 is worn on the face 31 by the person.

The display control section 11a housed in the circuit housing section 17 gives a video signal processed by the control section 11 to the display section 13. The display section 13 emits video light based on the video signal toward the incident surface of the light guide section 13b from the display panel 13a. The video light is guided in the light guide section 13b and emitted from the emission surface. In this way, an image based on the video signal from the control section 11 is visually recognized in a part of a field-of-view range of the right eye 32.

Note that the eyeglass-type terminal device is configured not to prevent an observation target from being directly observed in a see-through manner and to make it possible to simultaneously observe the directly-observed observation target and the image based on the inputted video signal seen in a part of the field-of-view range. For example, during various kinds of work, the user wearing the wearable unit 10, which is the eyeglass-type terminal device, is capable of directly observing a state of the work and, at the same time, observing a picked-up image acquired by the image acquiring section 12a or the like. Moreover, since the wearable unit 10 is a hand-free device, motions of hands and feet are not limited in the work and the observation. Therefore, it is possible to observe an image acquired by the image acquiring section 12a without spoiling workability achieved by making full use of both hands.

The display section 13 makes it possible to visually recognize a picked-up image acquired by the image acquiring section 12a with the light guide section 13b disposed in front of a right eye 32R of the face 31 as shown in FIG. 3. Broken lines respectively surrounding the right eye 32R and a left eye 32L in FIG. 3 indicate visual fields by the right and left eyes 32R and 32L.

Figure 4:
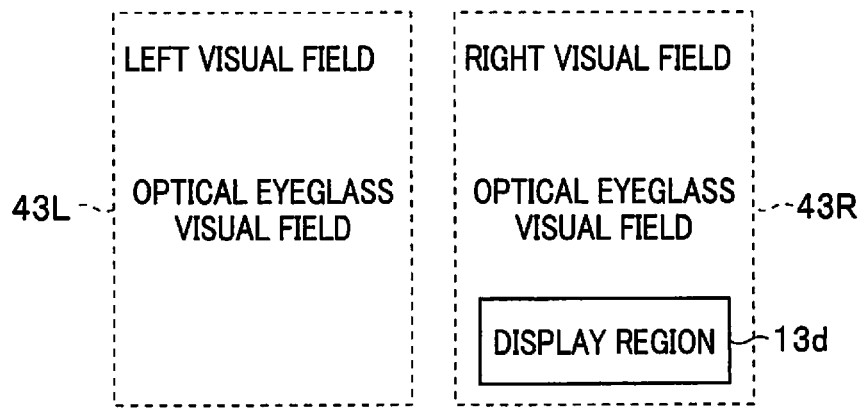
FIG. 4 is an explanatory diagram for explaining a visual field of an eyeglass-type terminal device.

FIG. 4 is an explanatory diagram for explaining the visual field. A left visual field 43L indicates a visual field by the left eye 32L. A right visual field 43R indicates a visual field by the right eye 32R. The left visual field 43L is an optical eyeglass visual field passed through a not-shown left lens (which may be transparent glass, or glass may be absent). The right visual field 43R is an optical eyeglass visual field passed through a not-shown right lens (which may be transparent glass, or glass may be absent). A display region 13d by the light guide section 13b is provided in a part of the right visual field 43R.

The optical eyeglass visual fields in the left and right visual fields 43L and 43R indicate an observation target that an operator wearing the wearable unit 10 actually views. The display region 13d is an image acquired by the image acquiring section 12a of the wearable unit 10. Therefore, the operator wearing the wearable unit 10 can observe, while confirming a work target or the like with the naked eye and making full use of both the hands to perform work requiring attention, a picked-up image of the work target in the display region 13d.

Note that an example is explained above in which the wearable unit 10 is configured by the eyeglass-type terminal device and worn on the head of the user. However, as the wearable unit 10, a device worn on a portion other than the head may be adopted.

Figure 6:
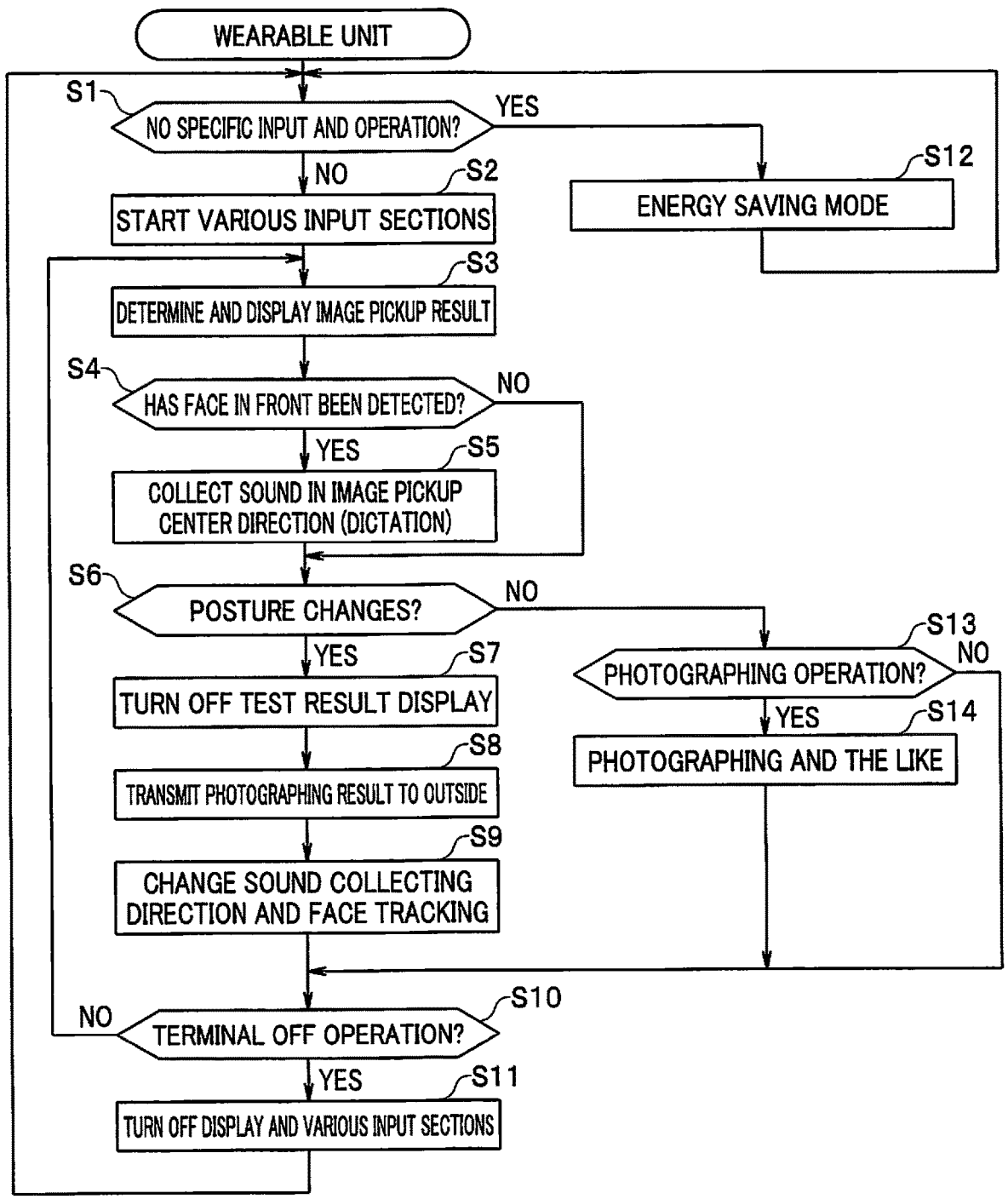
FIG. 6 is a flowchart for explaining the operation in the first embodiment.
Figure 7:
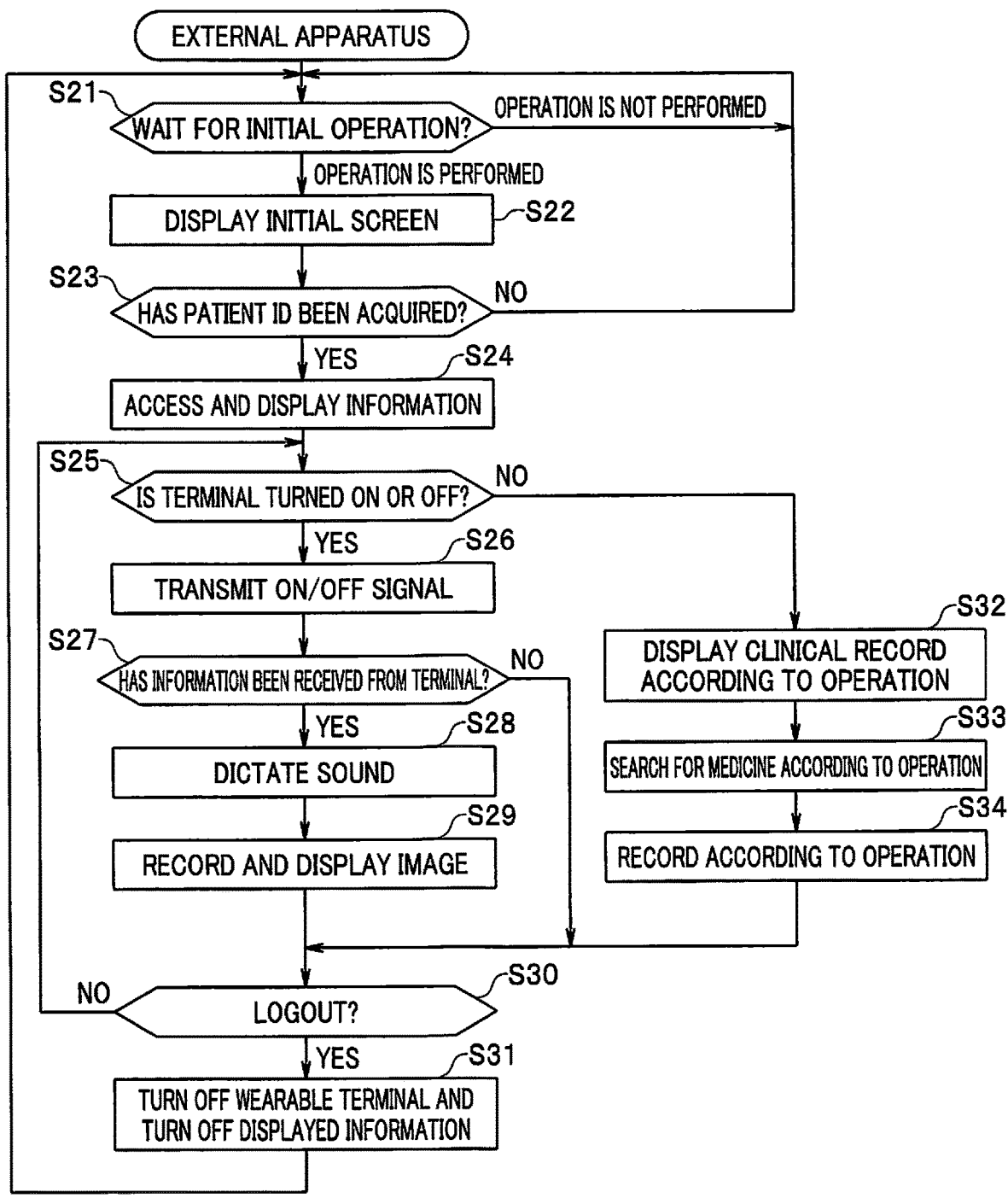
FIG. 7 is a flowchart for explaining the operation in the first embodiment.

Operation in the embodiment configured as explained above is explained with reference to FIGS. 5A to 5D, 6, and 7. FIGS. 5A to 5D are explanatory diagrams for explaining the operation in the first embodiment. FIGS. 6 and 7 are flowcharts for explaining the operation in the first embodiment.

Figure 5A:
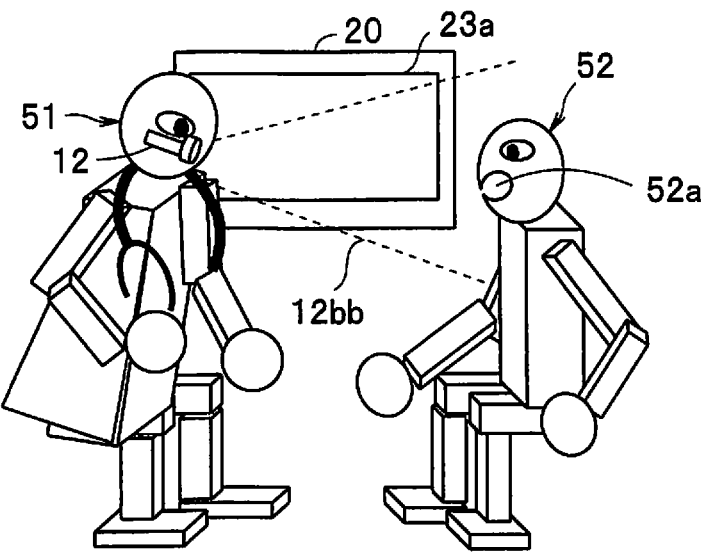
FIG. 5A is an explanatory diagram for explaining operation in the first embodiment.

FIGS. 5A to 5D show an example in which the wearable unit 10 in the present embodiment is adopted in a medical site. FIG. 5A shows a state in which a doctor 51 and a patient 52 sit on not-shown chairs while facing each other. The doctor 51 wears the wearable unit 10 shown in FIG. 2 and the like on a head. In FIG. 5A, the information acquiring section 12 of the wearable unit 10 is disposed on a right side of the head of the doctor 51. The external apparatus 20 is disposed on the left of the doctor 51. For medical practitioners such as a doctor, handling of various instruments, implements, and information terminals and contact with a patient are important. In many situations, it is more efficient to utilize a wearable device such that both hands can be used. However, attention should be paid to a fact that, although the wearable device or a device worn and used by a user has a desirable relation with the user, other relations such as a positional relation between the user and the patient are sometimes unstable depending on a posture, a motion, and behavior of the user.

A situation is assumed in which the doctor desires to give an explanation to the patient using an image of a diagnosed region. The doctor 51 acquires, with the information acquiring section 12, as an image, a state of the patient 52 seen by the doctor 51. The doctor 51 faces the patient 52, observes, for example, a tongue 52a of the patient 52, and diagnoses the patient 52's illness. At the time, the doctor 51 can see a state of the tongue 52a but the patient 52 cannot see the state. Therefore, the patient 52 cannot understand how to see the state well. Visualization of information is important for the patient 52 to receive an explanation concerning which region has a trouble, how bad the trouble is, and how the trouble is considered to be cured.

In step S1 in FIG. 6, the control section 11 of the wearable unit 10 determines whether a specific input signal or input operation for starting the wearable unit 10 is generated. When the specific input signal or input operation is not generated, in step S12, the control section 11 sets a power saving mode (an energy saving mode) and returns processing to step S1. In the power saving mode, the control section 11 performs control to supply electric power of the battery 15 only to a part of the wearable unit 10. In order to reduce a load during wearing of a wearable device, design for reducing size and weight of a battery and frequently reducing unnecessary energy consumption is important.

On the other hand, in the external apparatus 20, the control section 21 determines whether initial operation is performed in step S21 in FIG. 7. The control section 21 is in a standby state in which the control section 21 repeats the determination in step S21 until the initial operation is performed. When the initial operation is performed, in step S22, the control section 21 displays an initial screen on the display section 23. The initial screen displays various menus concerning treatment of respective patients. It is possible to access information of an individual patient by inputting a patient ID.

In step S23, the control section 21 determines whether a patient ID is inputted. Note that the patient ID can be designated by operation by the operation input section, operation on the touch panel on the display section 23, a sound input, or the like. For the sound recognition or the like, if the wearable device is worn, it is possible to clearly determine a sound in lips of the user. Usefulness of the wearable device is seen. It is possible to design, using a circuit and software having high energy saving properties, even before the wearable unit 10 starts, the wearable unit 10 to respond to only a specific sound and to be capable of starting with the specific sound even if sound acquisition performance of a microphone is low. When the patient ID is not inputted, the control section 21 returns the processing to step S21. When the patient ID is inputted, the control section 21 reads out information concerning a patient designated by the patient ID from a not-shown database and displays the information (step S24).

Subsequently, the control section 21 shifts the processing to step S25 and determines whether operation (ON) for starting the wearable unit 10 or operation (OFF) for stopping the start is performed. For example, it is possible to control ON and OFF of the wearable unit 10 with the operation input section or the touch panel of the external apparatus 20, the sound input, or the like. When the ON operation is not performed, the control section 21 shifts the processing to step S32, causes the display section 23 to display a medical record according to menu operation, performs a medicine search on the basis of user operation (step S33), updates the medical record according to the user operation, and records the medical record in the recording section (step S34). When the ON operation of the wearable unit 10 is performed, the control section 21 shifts the processing from step S25 to step S26 and transmits a signal for turning on the wearable unit 10 to the control section 11 via the communication sections 24 and 14. Note that, when the OFF operation of the wearable unit 10 is performed, the control section 21 shifts the processing from step S25 to step S26 and transmits a signal for turning off the wearable unit 10 to the control section 11 via the communication sections 24 and 14. When the medicine search or the like is performed by sound recognition using a wearable microphone, narrowing-down from various candidates is necessary. Performance of the microphone is increased to perform high-fidelity sound collection. Sound determination of answers and the like of the patient may be performed. In this case, if the microphone performance including noise cancellation is not good, correct recognition cannot be performed.

When determining in step S1 that some input operation for starting the wearable unit 10 is performed, the control section 11 of the wearable unit 10 shifts the processing to step S2, supplies electric power of the battery 15 to the respective sections, and starts the respective sections. Note that the control section 11 may shift the processing from step S1 to step S2 according to not only the operation by the external apparatus 20 but also a sound input to the sound acquiring section 12b. The embodiment uses the result of the sound recognition on the basis of the sound collected by the microphone of the wearable unit 10 for such an operation and a search. However, the result of the sound recognition by the microphone placed near a monitor of the external apparatus 20 may be used. However, in this case, a recognition rate is increased when the user views the monitor. Therefore, a positional relation between the wearable device and the patient changes. However, a system is provided that copes with such a situation without a problem.

The information acquiring section 12 of the wearable unit 10 worn by the doctor 51 picks up an image of a front of a face of the doctor 51 with the image acquiring section 12a. Note that a photographing range by the image acquiring section 12a is a relatively wide angle. The picked-up image acquired by the image acquiring section 12a is given to the display section 13 by the display control section 11a and displayed (step S3). The picked-up image given from the image acquiring section 12a is supplied to the range switching section 11b as well. In step S3, the range switching section 11b performs an image analysis of the picked-up image. Note that the display control section 11a may give the picked-up image acquired by the image acquiring section 12a to the display section 13 and cause the display section 13 to display the picked-up image or may give the picked-up image to the control section 21 of the external apparatus 20 via the communication sections 14 and 24 and cause the display section 23 to display the picked-up image. In this case as well, since the doctor, who is the user, views the display section 23, the positional relation between the wearable device and the patient changes. However, a system is provided that copes with such a situation without a problem. In this case, a movement of the patient is considered to be small.

In step S27, the control section 21 of the external apparatus 20 determines whether information from the wearable unit 10 is received. When information is not received, the control section 21 shifts the processing from step S27 to step S30. When information is received, the control section 21 shifts the processing to step S28. When the received information is a sound, the control section 21 performs dictation processing and records text information in the recording section 25. When the received information is an image, in step S29, the control section 21 gives the picked-up image to the display section 23 and causes the display section 23 to display the picked-up image and, at the same time, gives the picked-up image to the recording section 25 and causes the recording section 25 to record the picked-up image.

In step S4, the range switching section 11b of the wearable unit 10 performs an image analysis and determines whether a face of the patient 52 is detected in front of the doctor 51. When the face of the patient 52 is detected in the center of the picked-up image, the range switching section 11b sets a portion of the face, a portion of a mouth, and the like as a tracking target object. In this case, the range switching section 11b matches directivity of the sound acquiring section 12b to an image pickup center direction, which is a direction of the face of the doctor 51, and controls the directivity (step S5). The range switching section 11b sets a direction of the directivity during the tracking target object setting as a reference direction.

The sound acquiring section 12b of the information acquiring section 12 acquires a sound around the sound acquiring section 12b. The sound acquiring section 12b has directivity. In the state shown in FIG. 5A, the beam direction is a face direction of the patient 52. A range around the face has relatively high sensitivity. In FIG. 5A, a range 12bb having relatively high sensitivity is indicated by a broken line.

The sound acquired by the information acquiring section 12 is supplied to the control section 11. The control section 11 can execute the dictation processing for generating the text information with sound recognition processing for the inputted sound. The text information acquired by the dictation processing is transferred to the control section 21 via the communication sections 14 and 24 and recorded in the recording section 25 by the control section 21. Note that, as explained above, the control section 11 may directly transfer the sound to the control section 21 via the communication sections 14 and 24. The control section 21 may execute the dictation processing. In this way, close communication between the doctor and the patient is converted into characters and recorded as a document, whereby it is possible to perform correct diagnosis and verification.

Figure 5B:
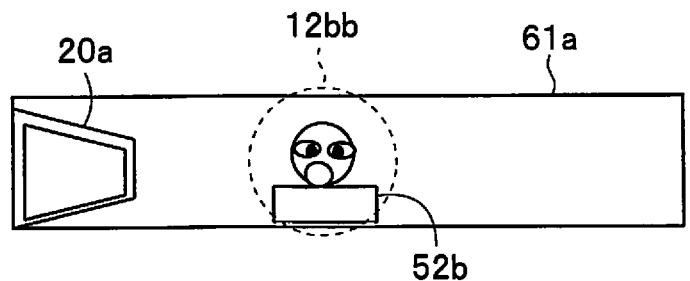
FIG. 5B is an explanatory diagram for explaining the operation in the first embodiment.

FIG. 5B shows a picked-up image 61a acquired by the image acquiring section 12a in the state shown in FIG. 5A. Note that the picked-up image 61a is used for directivity control of the sound acquiring section 12b. The picked-up image 61a may be displayed on the display section 13 of the wearable unit 10 or may be not displayed. The picked-up image 61a may be given to the display section 23 of the external apparatus 20. The picked-up image 61a may be directly displayed or a part of the picked-up image 61a may be enlarged and displayed. Note that an image 52b near the head of the patient 52 is included in a center of the picked-up image 61a. An image 20a of the external apparatus 20 is included at a left end portion of the picked-up image 61a. Note that the circular range 12bb indicated by a broken line in the picked-up image 61a indicates a range having relatively high sensitivity by the sound acquiring section 12b (a sound collection range by directivity).

In an example shown in FIG. 6, a tracking target object is automatically set in a face portion or the like located in front of the doctor 51. However, the control section 11 or the control section 21 may set the tracking target object on the basis of user operation. For example, in a state in which the picked-up image 61a is displayed on the display section 23, when the doctor 51 or the like touches the image 52b of the patient on the picked-up image 61a of the display section 23, the control section 21 may set the image 52b and a portion of the face and a portion of the mouth in the image 52b as the tracking target object. In this case, the control section 21 transmits information concerning the set tracking target object to the range switching section 11b via the communication sections 24 and 14.

In step S6, the range switching section 11b determines whether a posture of the doctor 51 changes. For example, the range switching section 11b detects with an image analysis of the picked-up image acquired by the image acquiring section 12a whether the posture of the doctor 51 changes. The explanation is based on the premise that a posture (behavior, etc.) of the user is a main factor of a relative position change with respect to the target object. Therefore, in order to guarantee the premise, first, the range switching section 11b may determine in the image given from the image acquiring section that the target object is present in the same position in a background. In this case, the range switching section 11b only has to detect a characteristic portion, for example, a face, of the target object, set an image around the face as a background, and determine that a relation between the background and the target object does not temporally change. In recent years, a compound eye camera and an image pickup device capable of performing distance distribution determination of a phase difference scheme have been developed. A distance distribution and the like of a situation are seen. Therefore, it may be detected that no change in the distance distribution occurs and determined that no or little change of the target object exist. If the relation between the background and the object can be grasped from the image, the temporal change in the distance distribution, and the like and the relation does not greatly change, it may be considered that a target of compensation of a movement is a movement of the user. The movement of the user may be specified solely as a rotational movement. A movement that could occur at that point may be assumed according to a wearing part, assumed work or job at that time, or the like and movement compensation control may be performed.

When the posture of the doctor 51 does not change, in step S13, the control section 11 determines presence or absence of photographing operation. Note that the range switching section 11b may determine only when the posture of the doctor 51 changes by a predetermined threshold angle or more that the posture of the doctor 51 changes. When the doctor 51 instructs photographing with operation of the not-shown operation section or a sound input, the image acquiring section 12a performs the photographing (step S14) and outputs a still image at photographing instruction timing. The still image is transferred to the control section 21 via the communication sections 14 and 24 and recorded in the recording section 25 by the control section 21.

Figure 5C:
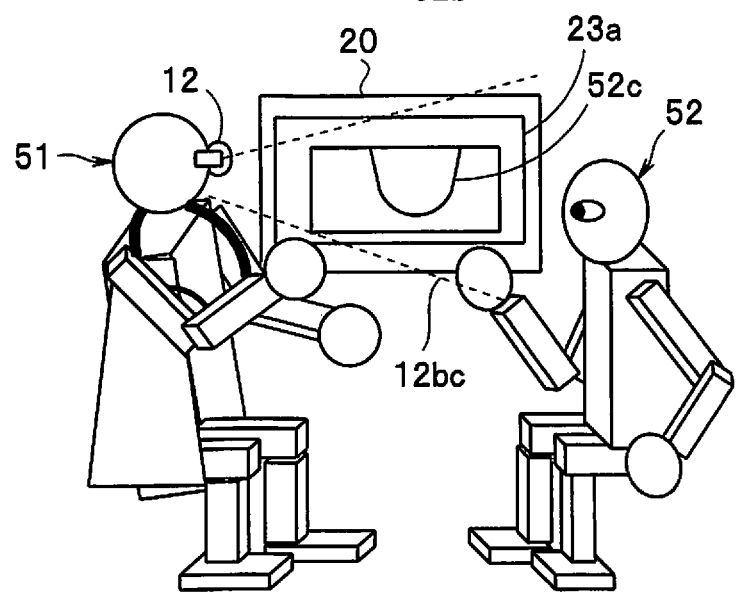
FIG. 5C is an explanatory diagram for explaining the operation in the first embodiment.

It is assumed that the posture of the doctor 51 changes. FIG. 5C shows a state in this case. An example shown in FIG. 5C indicates that, for example, the doctor 51 is giving an explanation concerning diagnosis to the patient 52 while viewing an image displayed on the display section 23 of the external apparatus 20. The doctor 51 changes a direction of the face to a left direction from a state in which the doctor 51 is viewing the face of the patient 52 sitting in front of the doctor (FIG. 5A) and directs the face to a direction of the display section 23 of the external apparatus 20. In this case, the picked-up image by the image acquiring section 12a also changes.

Figure 5D:
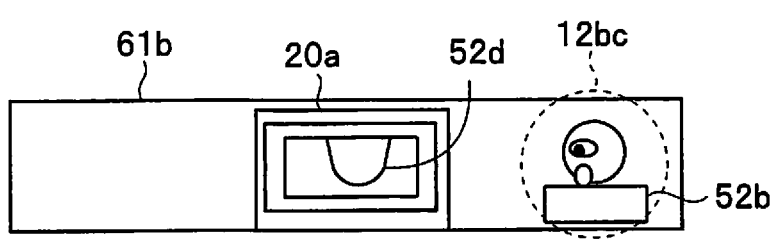
FIG. 5D is an explanatory diagram for explaining the operation in the first embodiment.

FIG. 5D shows a picked-up image 61b acquired by the image acquiring section 12a in the state shown in FIG. 5C. The face of the doctor 51 faces a direction of the external apparatus 20. The image 20a of the external apparatus 20 is included in a center of the picked-up image 61b. The image 52b near the head of the patient 52 is included at a right end portion of the picked-up image 61b.

The range switching section 11b calculates, with an image analysis of the picked-up image, a present direction from the sound acquiring section 12b to the tracking target object and calculates an angle from the reference direction to the present direction (hereinafter referred to as tracking angle). For example, the range switching section 11b may calculate an amount of angle switching for tracking on the basis of a change in a position on the picked-up image of the tracking target object.

When determining in step S6 that the posture of the doctor 51 changes, the range switching section 11b shifts the processing to step S7. In this case, the picked-up image by the image acquiring section 12a does not include a picked-up image of the patient 52. Therefore, the range switching section 11b turns off display of the picked-up image of the image acquiring section 12a, that is, a test result displayed on the display section 13. In this case, the display control section 11a reads out a picked-up image recorded in the recording section 16 immediately before the posture change of the doctor 51, gives the picked-up image to the control section 21 via the communication sections 14 and 24, and causes the display section 23 to display the picked-up image (step S8).

In this way, in this case, as shown in FIG. 5C, an image 52c of a throat and a tongue of the patient 52 is displayed on a display screen 23a of the display section 23. The image acquiring section 12a picks up an image in the display section 23 direction. As shown in FIG. 5D, in the picked-up image 61b, an image 52d of the throat and the tongue is included in the image 20a of the external apparatus 20.

In step S9, the range switching section 11b corrects the beam direction by the tracking angle and generates a control signal to match the beam direction with a present tracking target object direction. The control signal is supplied to the sound acquiring section 12b. The sound acquiring section 12b changes the beam direction to the present tracking target object direction, that is, a direction of the face portion and the mouth portion of the patient 52.

In this way, the sound acquiring section 12b can always direct the beam direction to the direction of the tracking target object. It is possible to surely acquire a sound from the tracking target object direction.

In step S10, the control section 11 determines whether terminal OFF operation is performed. When the terminal OFF operation is not performed, the control section 11 returns the processing to step S3. When the terminal OFF operation is performed, the control section 11 stops the power supply to the respective sections of the wearable unit 10 and turns off the display of the display section 13 (step S11).

Note that, in step S30, the control section 21 of the external apparatus 20 determines whether logout operation is performed. When the logout operation is not performed, the control section 21 shifts the processing to step S25. When the logout operation is performed, the control section 21 shifts the processing to step S31, turns off the wearable unit 10, and turns off the display of the display section 23.

Note that, in the flows shown in FIGS. 6 and 7, it is explained that the tracking target object is present within the image pickup range of the image acquiring section 12a even when the doctor 51 changes the posture. However, it is also likely that the tracking target object deviates from the image pickup range depending on a change amount of the posture of the doctor 51. Therefore, in this case, a direction of the tracking target object present in the image pickup range last is fixed to the tracking angle from the reference direction. The directivity of the sound acquiring section 12b is controlled on the basis of the tracking angle. When the tracking target object is present (captured) in the image pickup range again, the tracking angle is calculated on the basis of a position on the picked-up image of the tracking target object in that case to control the directivity of the sound acquiring section 12b.

At the time, a positional relation between the patient and the user changes because of various factors such as a movement of the patient and a movement of the user and could affect a sound collection characteristic. However, this explanation is based on the premise that a problem occurs because of a posture, a motion, and behavior of the user, who is the doctor, including a characteristic of a situation. It is sometimes necessary to consider whether a movement of the user is predominant or a movement of the target (the patient) is predominant. For example, it is unnecessary to track the patient until the patient exits a room. At that time, conversation with a nurse or a supporter is sometimes more important. Note that, in this way, it is possible to determine whether the movement of the user is predominant or the movement of the target object is predominant according to whether the target object and the background are present in the relatively same positions. When the target object is present in the same place in this way, a posture change of the user can be determined according to from where to where in the picked-up image a tracking image moves. That is, in the present invention, it may be determined that the position of the target object does not change even if a relative relation between the sensor and the target object changes. As the method, it may be detected and determined with the camera of the wearable device that the position of the target object does not change, a monitoring camera or a monitor camera such as a camera for PC may be provided on an outside to receive a result obtained by determining that the position of the patient does not change and determine that the position of the target object does not change, or a sensor for determining a movement of a person like a human sensor may be provided to determine that the position of the target object does not change because an output of the sensor does not change. The determination is not limited to the determination in the image. A change in a distance distribution or the like may be determined. An apparatus such as a Drone determines a state of an environment from irradiation of laser light and reflection of the laser light. Such a technique may be used. In this way, it is possible to provide a sensor information acquiring device including the control section configured to control the information acquisition direction of the sensor on the basis of information concerning displacement of a displacement section to which the sensor is attached.

In this way, in the present embodiment, the tracking target object is set, the tracking angle, which is the change in the direction from the sound acquiring section to the tracking target object, is detected, and the beam direction is corrected by the tracking angle on the basis of the beam direction during the tracking target object setting. Consequently, it is possible to always direct the beam direction to the tracking target object and enable sure sound collection. The tracking target is determined using the information concerning the image acquired by the worn device. According to a change in the posture of the user wearing the wearable device, the sound collection range of a sound is switched by tracking the tracking target not to be affected by the change in the posture of the user wearing the wearable device. Besides, a state of the user may be photographed by a monitoring camera, a Web camera, or a camera incorporated in an information terminal. A posture change of the user may be determined with an image. Besides, a method of the tracking is not limited to the image. The determination of the posture of the user may be performed using an acceleration sensor, a direction sensor, an angular acceleration sensor, or the like. Further, a method of switching directivity of a microphone at high speed and selecting best directivity is also applicable.

Second Embodiment

Figure 8:
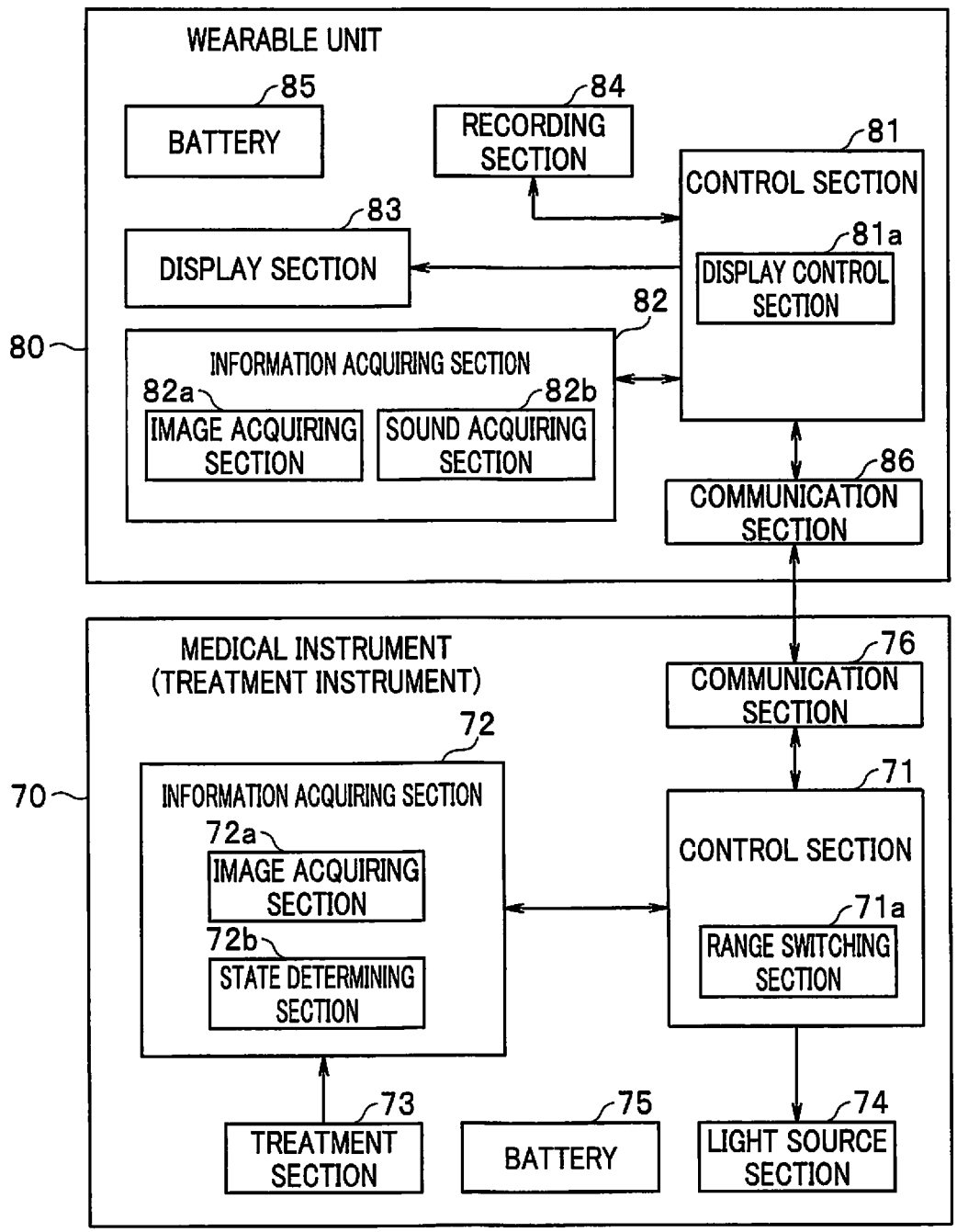
FIG. 8 is a block diagram showing a second embodiment of the present invention.

FIG. 8 is a block diagram showing a second embodiment of the present invention. In FIG. 8, the same components as the components shown in FIG. 1 are denoted by the same reference numerals and signs and explanation of the components is omitted.

In recent years, robot surgery is sometimes adopted in a medical site. In the robot surgery, an endoscope camera and a robot arm are inserted into a body and a doctor operates a handle in a hand to move the robot arm and perform surgery while watching a surgical field with an image on a console, which displays an image outputted from the endoscope camera. The robot surgery has an advantage that it is possible to surely control even a fine movement according to robot control.

However, even in the robot surgery, a staff member such as hemostasis personnel is necessary other than the doctor who operates a robot. Therefore, the robot and the staff member cross each other near a patient who receives treatment. Movements of the robot and the staff member are sometimes limited. The doctor needs to sufficiently become proficient in the robot operation.

Therefore, in the present embodiment, a medical instrument attachable to a fingertip of a surgeon is adopted. The medical instrument is controlled to acquire an image and continue to display a set tracking target object, for example, in a screen center to enable the surgeon to carry out treatment and the like while confirming a diseased part. Consequently, it is possible to sufficiently reduce influence on other staff members and influence from the other staff members and efficiently perform surgery and the like. Moreover, it is possible to perform work with the same feeling as surgery performed directly using fingers of the surgeon. It is possible to improve workability. It is unnecessary to perform long-term learning for the robot surgery.

FIG. 8 shows an example in which an information processing system is configured by a medical instrument 70 and a wearable unit 80. In the present embodiment, a target object (a tracking target object) of interest in image information acquired by a camera is set and a change in a direction from the camera to the tracking target object is detected by a predetermined sensor to perform display control such that, for example, the tracking target object is always displayed in a screen center. By displaying the target object of interest in the screen center, visibility of the target object of interest is sometimes improved. In this case, effective information is included in a portion displayed in the screen center. An information acquisition direction is also considered to be a direction toward the portion displayed in the screen center. In the present embodiment, even when a direction of the camera changes and an image pickup range changes, the information acquisition direction is changed in to a tracking target object direction to display the tracking target object in the screen center and make it easy to confirm the tracking target object. That is, it is possible to prevent visibility of the tracking target object from being deteriorated and improve workability irrespective of the direction of the camera.

The medical instrument 70 includes a not-shown locking section for attaching a housing incorporating a circuit shown in FIG. 8 to a part of a body of a user. The medical instrument 70 is movable according to a movement of the user, for example, a movement of fingers.

The medical instrument 70 includes a control section 71. The control section 71 controls respective sections of the medical instrument 70. The control section 71 may be configured by a processor in which a CPU or the like is used. The control section 71 may operate according to a computer program stored in a not-shown memory to control the respective sections. A part of the control section 71 may be replaced with a hardware electronic circuit.

A battery 75 is incorporated in the medical instrument 70. The battery 75 is controlled by the control section 71 to generate electric power supplied to the respective sections of the medical instrument 70. The medical instrument 70 includes a light source section 74 as well. The light source section 74 is controlled by the control section 71 to emit light with the power supply from the battery 75. The light source section 74 can illuminate a periphery of the medical instrument 70.

The medical instrument 70 includes an information acquiring section 72. The information acquiring section 72 acquires sensor information concerning a tracking target object that the user desires to photograph. The information acquiring section 72 includes, for example, an image acquiring section 72a and a state determining section 72b. The image acquiring section 72a can be configured by, for example, a not-shown image sensor. The image acquiring section 72a can pick up an image of the tracking target object and acquire a picked-up image. The image acquiring section 72a is configured to output the acquired picked-up image to the control section 71 as sensor information. In the present embodiment, a wide-angle lens is adopted by the image acquiring section 72a. Therefore, the image acquiring section 72a can acquire a wide-angle image.

In the present embodiment, the information acquiring section 72 is also used to acquire information concerning a direction of the tracking target object, which is a target object of a picked-up image that the image acquiring section 72a is about to acquire. A state determining section 72b is provided in the information acquiring section 72. The state determining section 72b is configured to detect displacement of a treatment section 73 and output information concerning the displacement of the treatment section 73, which is a displacement section, to a range switching section 71a of the control section 71. The treatment section 73 is an instrument for performing treatment on a subject such as forceps or an electric knife. Note that, although not shown in FIG. 8, when the electric knife is adopted as the treatment section 73, a signal wire for supplying high-frequency power from an electric knife device to the electric knife is wired. The control section 71 is configured to be capable controlling the power supply to the electric knife as well.

The range switching section 71a is configured to be capable of calculating a change amount of a field-of-view range in picked-up images before and after a change in the field-of-view range on the basis of information concerning the displacement of the treatment section 73. The range switching section 71a is configured to shift or zoom an image to generate a display image on the basis of information concerning the calculated change amount of the field-of-view range such that an image portion of the tracking target object is located in the screen center. The image acquiring section 72a is configured to acquire a wide-angle image having a sufficiently wide angle of view. Even when the field-of-view range of the image acquiring section 72a changes because the medical instrument 70 moves or changes a direction, it is highly likely that the image portion of the tracking target object included in the image pickup range before the field-of-view range change continues to be picked up. Therefore, by shifting or zooming the image by a change in the field-of-view range due to a movement of the medical instrument 70, it is possible to display the image portion of the tracking target object in the screen center. Note that the range switching section 71a may be configured to display the image portion of the tracking target object in a portion other than the screen center.

The control section 71 is configured to be capable of transmitting the display image generated by the range switching section 71a to the wearable unit 80 via a communication section 76.

The range switching section 71a may generate, on the basis of an output of the image acquiring section 72a, a display image corresponding to the displacement of the treatment section 73. A picked-up image by the image acquiring section 72a is given to the range switching section 71a of the control section 71. The range switching section 71a may find, with an image analysis of the picked-up image, the image portion of the tracking target object included in the picked-up image before the field-of-view range change out of the picked-up image after the field-of-view range change and shift or zoom the picked-up image to generate a display image such that the image portion is located in the screen center.

The range switching section 71a is configured to be capable of setting a tracking target object. For example, the range switching section 71a may set, on the basis of user operation for designating acquisition timing, as the tracking target object, an image portion in a center of the picked-up image given from the image acquiring section 72a. For example, the range switching section 71a may set, as the acquisition timing, timing when a not-shown button provided in a treatment instrument is operated or may set, as the acquisition timing, timing when a state of the treatment section 73 is a predetermined state and set the tracking target object. For example, the range switching section 71a may be configured to receive designation operation for the tracking target object by the user and perform setting of a target section. For example, the range switching section 71a may cause a not-shown operation section to display a pointer on an image in a state in which the picked-up image acquired by the image acquiring section 72a is displayed on a display screen of a display section 83 explained below of the wearable unit 80 and, when a portion on the image is designated by the user with the pointer, set the image portion as the tracking target object. For example, when detecting designation operation for a specific portion on the image, the range switching section 71a may set, as the tracking target object, a target object in a predetermined range including the designated image portion.

The communication section 76 is provided in the medical instrument 70. The communication section 76 is controlled by the control section 71 to be capable of performing communication by wire or radio between the communication section 76 and the wearable unit 80. For example, the communication section 76 can be configured by various controllers corresponding to a transmission line between the communication section 76 and the wearable unit 80. For example, a LAN controller is adopted as the communication section 76 when the LAN cable is adopted as the transmission line. A wireless LAN controller is adopted as the communication section 76 when Wi-Fi is adopted as the transmission line. A USB controller is adopted as the communication section 76 when the transmission line is a USB cable. A video controller is adopted as the communication section 76 when the transmission line is a video cable.

In the present embodiment, an eyeglass-type terminal device or the like can be adopted as the wearable unit 80. The wearable unit 80 includes a control section 81. The control section 81 controls respective sections of the wearable unit 80. The control section 81 may be configured by a processor in which a CPU or the like is used. The control section 81 may operate according to a computer program stored in a not-shown memory to control the respective sections. A part of the control section 81 may be replaced with a hardware electronic circuit.

A communication section 86 is provided in the wearable unit 80. The communication section 86 is controlled by the control section 81 to be capable of performing communication by wire or radio between the communication section 86 and the medical instrument 70. For example, the communication section 86 can be configured by various controllers corresponding to a transmission line between the communication section 86 and the medical instrument 70. For example, a LAN controller is adopted as the communication section 86 when a LAN cable is adopted as the transmission line. A wireless LAN controller is adopted as the communication section 86 when Wi-Fi is adopted as the transmission line. A USB controller is adopted as the communication section 86 when the transmission line is a USB cable. A video controller is adopted as the communication section 86 when the transmission line is a video cable.

A display control section 81*a* is provided in the control section 81. The display control section 81*a* executes various kinds of processing concerning display. The display control section 81*a* can be configured by, for example, a video controller or a display controller. The display control section 81*a* may be configured separately from the control section 81. The display control section 81*a* controls display of the display section 83. The display section 83 includes a display screen such as an LCD and displays an image given from the display control section 81*a*. For example, when a picked-up image given from the image acquiring section 72*a* is transmitted via the communication sections 76 and 86, the display control section 81*a* can cause the display section 83 to display the picked-up image on the display screen of the display section 83.

The wearable unit 80 includes an information acquiring section 82. The information acquiring section 82 acquires sensor information around the wearable unit 80. The information acquiring section 82 includes, for example, an image acquiring section 82*a* and a sound acquiring section 82*b*. The image acquiring section 82*a* can be configured by, for example, a not-shown image sensor. The image acquiring section 82*a* can acquire a picked-up image in a predetermined image pickup range. The image acquiring section 82*a* is configured to output the acquired picked-up image to the control section 81 as sensor information. The display control section 81*a* can also cause the display section 83 to display the picked-up image outputted from the image acquiring section 82*a*.

The sound acquiring section 82*b* can be configured by, for example, a microphone. The sound acquiring section 82*b* can acquire a sound around the sound acquiring section 82*b*. The sound acquiring section 82*b* can supply the acquired sound to the control section 81. The control section 81 can acquire, with dictation processing, text information of the acquired sound. Consequently, the control section 81 can interpret a sound command by the user and receive operation by a sound.

A recording section 84 is provided in the wearable unit 80. The recording section 84 is controlled by the control section 81 to be capable of recording, in a not-shown recording medium such as a memory, the image and the sound acquired in the information acquiring section 72 and 82. The recording section 84 is configured to be capable of reading out and reproducing the image and the sound recorded in the not-shown recording medium and outputting the reproduced image and the reproduced sound to the control section 81. Consequently, the control section 81 is capable of causing, for example, the display section 83 to display the image recorded by the recording section 84.

A battery 85 is incorporated in the wearable unit 80. The battery 85 is controlled by the control section 81 to generate electric power supplied to the respective sections of the wearable unit 80.

Figure 9:
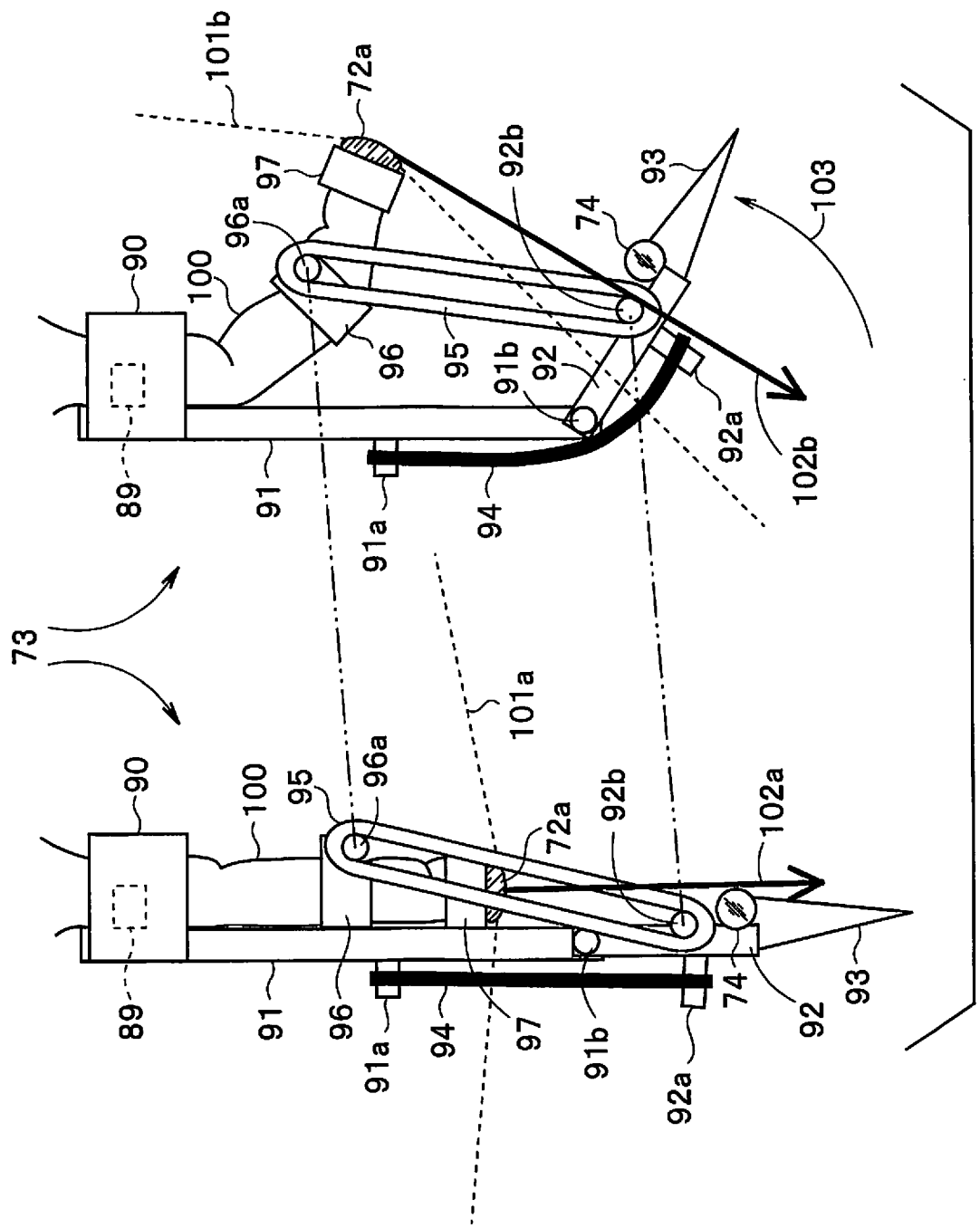
FIG. 9 is an explanatory diagram showing an exterior of a medical instrument 70 in FIG. 8.

FIG. 9 is an explanatory diagram showing an example of the medical instrument 70 in FIG. 8. A left side of FIG. 9 shows the treatment section 73 in a case in which a finger is stretched. A right side of FIG. 9 shows the treatment section 73 in a case in which the finger is bent.

FIG. 9 shows an example in which the medical instrument 70 is configured by a treatment instrument including a function of an electric knife. The treatment section 73 includes a first frame 91 and a second frame 92. On a proximal end side of the first frame, an insertion section 90 for inserting a finger of a surgeon and supporting the first frame 91 on a proximal end side of the finger is attached. A circuit section 89 on which the respective sections of the control section 71, the information acquiring section 72, the battery 75, and the communication section 76 in the medical instrument 70 shown in FIG. 8 are mounted is provided in the insertion section 90.

On a distal end side of the first frame, a driving shaft 91*b* is attached. The second frame 92, a proximal end side of which is turnably supported by the driving shaft 91*b*, is provided. An electric knife 93 is attached to a distal end side of the second frame 92. The electric knife 93 is connected to the circuit section 89 by a not-shown wire, which is inserted through the second frame 92 and the first frame 91, and driven. The light source section 74 is also attached to the distal end of the second frame 92. The light source section 74 receives power supply from the battery 75 by a not-shown wire, which is inserted through the second frame 92 and the first frame 91, and applies illumination light on a subject.

A locking section 91*a* is provided on a side portion of the first frame 91. A locking section 92*a* is provided on a side portion of the second frame 92. An urging member 94 is laid over the locking section 91*a* and the locking section 92*a*. As the urging member 94, an elastic material such as a spring or rubber is adopted. The urging member 94 urges the locking section 92*a* to the locking section 91*a* side. With an urging force of the urging member 94, as shown on the left side of FIG. 9, the first frame 91 and the second frame 92 are substantially linearly disposed. Note that, as explained below, the second frame 92 can also be disposed in a state inclined with respect to the first frame resisting the urging force of the urging member 94 by a motion of bending a finger 100.

A not-shown rotary encoder is disposed in the driving shaft 91*b*. The rotary encoder is configured to be capable of acquiring information concerning an inclination angle of the second frame 92 with respect to the first frame 91. The rotary encoder is configured to output the acquired information concerning the inclination angle to the state determining section 72*b* on the circuit section 89 via a not-shown wire inserted through the first frame 91. Consequently, the state determining section 72*b* can acquire information concerning the displacement of the treatment section 73.

As the treatment section 73, a fitting section 96, into which a finger of the surgeon is inserted, fit in a position near a second joint of the finger is also provided. A shaft member 96*a* is provided on a side portion of the fitting section 96. A shaft member 92*b* is provided on a side portion of the second frame 92. An annular member 95 is attached to the shaft members 96*a* and 92*b*. The annular member 95 is capable of rotating along circumferential surfaces of the shaft members 96*a* and 92*b* in portions of the shaft members 96*a* and 92*b*. A distance between the shaft members 96*a* and 92*b* is maintained at a constant distance according to size of the annular member 95.

The surgeon inserts the finger 100 into the insertion section 90 from a proximal end side of the first frame 91, further inserts the finger 100 into the fitting section 96, and wears the treatment section 73 such that the fitting section 96 is located in a vicinity of a second joint. When the surgeon stretches the finger 100 in the state, the state changes to a state on the left side of FIG. 9. When the surgeon bends the finger 100, the second frame 92 and the electric knife 93 move as indicated by an arrow 103 in FIG. 9 and the state changes to a state on the right side of FIG. 9. An angle of the electric knife 93 with respect to the first frame 91 changes according to an angle of the bending of the finger 100. The surgeon can change the angle of the electric knife 93 with a simple motion of bending the finger 100. The surgeon can freely change a position and the angle of the electric knife 93 and easily perform excision and the like of an organism by moving the finger 100 to a desired position, changing a direction of the finger 100 to a desired position, and bending the finger 100 by a desired angle.

An annular fitting member 97 is fit in a tip of the finger 100 of the surgeon. In the fitting member 97, the image acquiring section 72a is disposed on a fingertip end side. As explained above, the image acquiring section 72a is capable of performing image pickup at a relatively wide angle. In FIG. 9, angles of view 101a and 101b of the image acquiring section 72a are indicated by broken lines.

As explained above, the range switching section 71a may set a tracking target object with a picked-up image in a case in which the state of the treatment section 73 is the predetermined state. For example, the range switching section 71a may set, as the tracking target object, a center portion of a picked-up image of the image acquiring section 72a in a case in which the finger 100 is stretched to be substantially linear, that is, the first frame 91 and the second frame are substantially linearly disposed.

In the state on the left side of FIG. 9, a direction indicated by a thick line arrow 102a is a center direction of an angle of view. In this case, it is assumed that a subject portion in a direction indicated by the thick line arrow 102a is set as the tracking target object. In this case, the range switching section 71a generates, on the basis of information concerning the displacement of the treatment section 73 received from the state determining section 72b, a display image in which an image portion of the tracking target object in the thick line arrow 102a direction in the picked-up image of the image acquiring section 72a is disposed in a screen center.

For example, it is assumed that, the surgeon bends a finger in a state in which the forger is stretched, whereby the treatment section 73 is displaced from the state on the left side of FIG. 9 to the state on the right side of FIG. 9. In this case, the image acquiring section 72a picks up an image of a range of the angle of view 101b. The range of the angle of view 101b includes the subject (the tracking target object) in the thick line arrow 102a direction on the left side of FIG. 9. A thick line arrow 102b direction on the right side of FIG. 9 indicates a direction of the tracking target object. That is, the image acquiring section 72a is capable of picking up an image of the subject, which is the tracking target object, within the range of the angle of view 101b. The range switching section 71a shifts or zooms an image portion in the thick line arrow 102a direction in the picked-up image of the image acquiring section 72a to a screen center and generates a display image.

Figure 10:
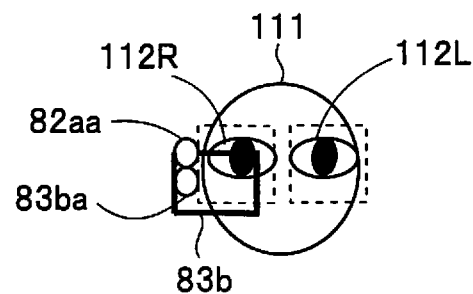
FIG. 10 is an explanatory diagram showing a positional relation between respective sections of a wearable unit 80 and a face.

FIG. 10 is an explanatory diagram showing a positional relation between the respective sections of the wearable unit 80 and a face. FIG. 10 shows an example in which an eyeglass-type wearable terminal device (an eyeglass-type terminal device) having the same configuration as the configuration shown in FIG. 2 is adopted as the wearable unit 80.

An image pickup lens 82aa configuring an image acquiring section 82a is disposed in the wearable unit 80. An optical image from an object is given to an image pickup device of the image acquiring section 82a via the image pickup lens 82aa. A picked-up image based on a subject optical image can be acquired by the image pickup device. For example, the image pickup lens 82aa is provided at a distal end of a temple portion of an eyeglass frame. The temple portion faces substantially the same direction as a face 111 of a person. Therefore, the image acquiring section 82a is capable of picking up an image of a subject in the same direction as an observation direction of human eyes 112R and 112L. Consequently, the image acquiring section 82a is capable of acquiring, as the picked-up image, an image corresponding to a work state in which a person is observing.

A microphone 82ba configuring the sound acquiring section 82b is disposed under the image pickup lens 82aa. A display surface 83b of the display section 83 is disposed on a front side of a right lens of left and right lenses of the eyeglass-type terminal device. The display surface 83b is disposed in a position corresponding to a part of a region of the right lens in a front of the right eye 112R in a state in which the person wears an eyeglass frame on the face 111.

The display control section 81a gives a video signal processed by the control section 81 to the display section 83. The display section 83 displays video light based on the video signal on the display surface 83b. In this way, an image based on the video signal given from the control section 81 is visually recognized in a part of a field-of-view range of the right eye 112R. Advice, state confirmation, OK display of treatment, and display of prohibition, warning, and the like can be displayed in the part of the field-of-view range according to necessity. In order to perform such display, the control section 81 may determine an image pickup result of the eyeglass-type terminal. The control section 71 on the treatment instrument side may use the determination by an information acquisition result (determination of attendance and absence, an abnormal movement, and the like).

Note that the eyeglass-type terminal device is configured not to prevent an observation target from being directly observed in a see-through manner and to make it possible to simultaneously observe the directly-observed observation target and the image based on the inputted video signal seen in a part of the field-of-view range. For example, during various kinds of work, the user wearing the wearable unit 80, which is the eyeglass-type terminal device, is capable of directly observing a state of the work and, at the same time, observing a picked-up image acquired by the image acquiring section 72a or the like of the medical instrument 70. Moreover, since the wearable unit 80 is a hand-free device, motions of hands and feet are not limited in the work and the observation. Therefore, it is possible to observe an image acquired by the image acquiring section 72a without spoiling workability achieved by making full use of both hands. Note that, to give due warning to avoid confusion, since the medical instrument 70 is also worn on the finger, the medical instrument 70 also has the characteristic of the wearable device. Although the eyeglass-type terminal and the treatment instrument (the medical instrument) are worn on separate places, the eyeglass-type terminal and the treatment instrument can be grasped as one device. If one common control section or the like exists, the common control section can be used as both of the control section 71 and the control section 81.

Note that broken lines respectively surrounding the right eye 112R and the left eye 112L in FIG. 10 indicate visual fields by the left and right eyes 112R and 112L.

Figure 11:
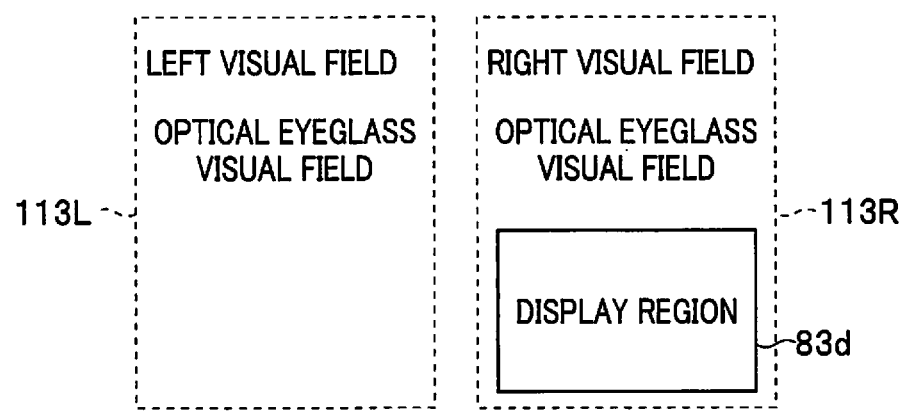
FIG. 11 is an explanatory diagram for explaining a visual field of an eyeglass-type terminal device.

FIG. 11 is an explanatory diagram for explaining the visual field. A left visual field 113L indicates a visual field by the left eye 112L. A right visual field 113R indicates a visual field by the right eye 112R. The left visual field 113L is an optical eyeglass visual field passed through a not-shown left lens (which may be transparent glass, or glass may be absent). The right visual field 113R is an optical eyeglass visual field passed through a not-shown right lens (which may be transparent glass, or glass may be absent). A display region 83d by the display surface 83b is provided in a part of the right visual field 113R. The display region 83d is set to a sufficiently large size to facilitate observation of a picked-up image by the image acquiring section 72a.

The optical eyeglass visual fields in the left and right visual fields 113L and 113R indicate an observation target that the surgeon views from, for example, an outer side of a body of a patient. The display region 83d indicates, for example, a tracking target object obtained by picking up an image of a diseased part in an abdominal cavity of a patient in a state in which the surgeon wears the medical instrument 70 on the finger 100. Therefore, an operator wearing the wearable unit 80 can observe, while confirming a work state of the finger 100 wearing the medical instrument 70 with the naked eye from the outer side of the body and making full use of both hands to perform work requiring attention, a picked-up image in the abdominal cavity of the work target in the display region 83d.

Figure 12:
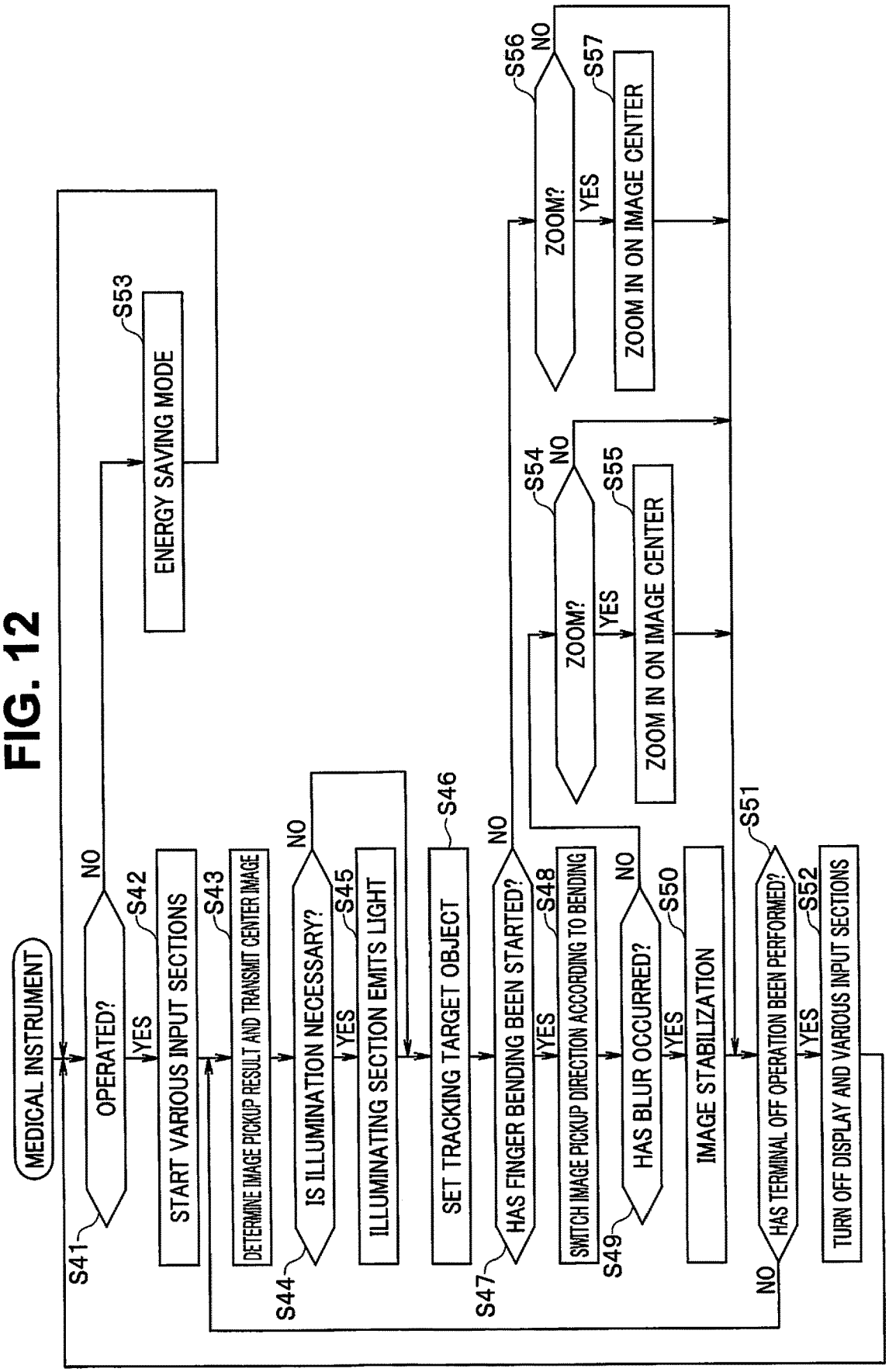
FIG. 12 is a flowchart for explaining operation in the second embodiment.
Figure 13:
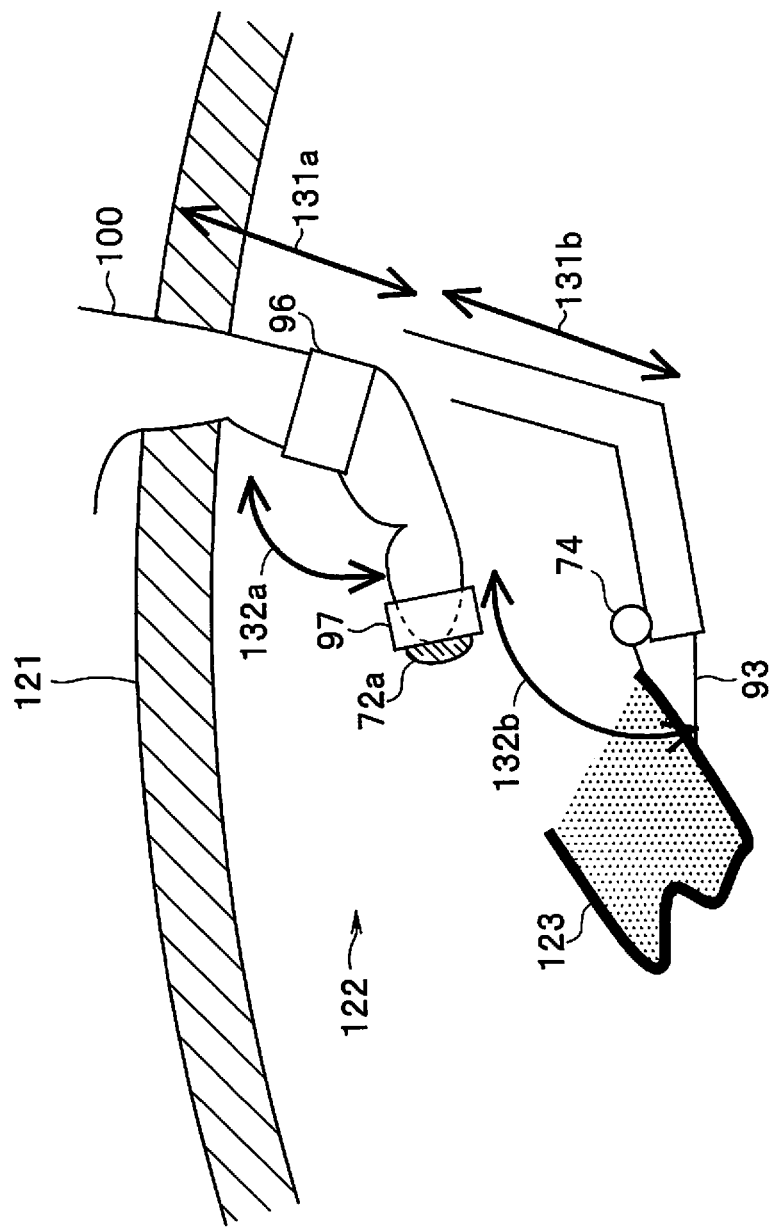
FIG. 13 is an explanatory diagram for explaining the operation in the second embodiment.

Operation in the embodiment configured as explained above is explained with reference to FIGS. 12 and 13. FIG. 12 is a flowchart for explaining the operation in the second embodiment. FIG. 13 is an explanatory diagram for explaining the operation in the second embodiment.

FIG. 13 shows an example in which treatment of the patient is performed using the medical instrument 70 in the present embodiment. An opening, into which the medical instrument 70 can be inserted, is formed on a patient body surface 121. The surgeon inserts the finger 100, on which the medical instrument 70 is worn, into a body cavity 122 via the opening on the patient body surface 121. By moving the finger 100 in an arrow 131a direction, it is possible to move the first frame 91 of the medical instrument 70 in an arrow 131b direction. Because of such a situation, various position changes predominantly occur because of an act (although a movement of the finger is shown as an example, a posture or behavior) of the user of the medical instrument 70. As a premise, the patient is substantially stationary.

In step S41 in FIG. 12, the control section 71 of the medical instrument 70 determines whether a specific input signal or input operation for starting the medical instrument 70 is generated. When the specific input signal or input operation is not generated, in step S53, the control section 71 sets a power saving mode (an energy saving mode) and returns processing to step S41. In the power saving mode, the control section 71 performs control to supply electric power of the battery 75 to only a part of the medical instrument 70.

When determining that ON operation for starting the medical instrument 70 is generated, the control section 71 shifts the processing to step S42, supplies the electric power of the battery 75 to the respective sections, and starts the respective sections. Note that the control section 71 may be configured to shift the processing from step S41 to step S42 according to a command notified from the control section 81 according to a sound input to the sound acquiring section 82b in the wearable unit 80.

The image acquiring section 72a disposed at the tip of the finger 100 picks up an image of an inside of the body cavity 122 at a wide angle. The picked-up image is supplied to the control section 71. The control section 71 directly sets the picked-up image as a display image or sets a center image as the display image and outputs the display image to the control section 81 of the medical instrument 70 via the communication sections 76 and 86 (step S43). The display control section 81a displays the picked-up image of the inside of the body cavity 122, for example, on the display section 83 of the eyeglass-type medical instrument 70.

In step S44, the control section 71 determines whether illumination is necessary. When the picked-up image does not have sufficient brightness, the control section 71 causes the light source section 74 to emit light (step S45). In this way, the inside of the body cavity 122 is illuminated by the light source section 74 provided on the distal end side of the medical instrument 70. The picked-up image by the image acquiring section 72a is an image excellent in visibility. Note that, when determining in step S44 that illumination is unnecessary, the control section 71 shifts the processing to step S46 without lighting the light source section 74 from the viewpoint of power saving.

In this way, the surgeon moves the finger 100 while viewing the picked-up image of the inside of the body cavity 122 displayed in the display region 83d by the display section 83 of the medical instrument 70 and moves the medical instrument 70 to a target part 123 to which treatment is applied, that is, to a vicinity of the tracking target object. The range switching section 71a sets, as the tracking target object, an image center portion of a picked-up image by the image acquiring section 72a in a case in which the finger 100 is stretched and the first frame 91 and the second frame 92 are substantially linear (step S46) and shifts the processing to step S47. Note that the range switching section 71a may set the tracking target object according to another method. For example, the range switching section 71a may set the tracking target object with operation for designating an image portion of the target part 123 in the picked-up image displayed on the display section 83 of the wearable unit 80.

The explanation is based on the premise that a movement (behavior, etc.) of the finger of the user is a main factor of a relative position change with respect to the target object. Therefore, in order to guarantee the premise, the range switching section 71a may first confirm a result obtained by determining in an image given from the image acquiring section that the target object is present in the same position in a background. A process for determining in an image pickup result that the image of the target part 123 does not move with a specific intra-body cavity pattern set as the background may be inserted. The explanation is based on the premise that a posture (behavior, etc.) of the user is a main factor of a relative position change with respect to the target object. Therefore, in order to guarantee the premise, the range switching section 71a may first determine in the image given from the image acquiring section that the target object is present in the same position in the background. In this case, the range switching section 71a only has to detect a characteristic portion, for example, a color or a shape of the target part 123, set an image around the color or the shape as a background, and determine that a relation between the background and the target part 123 does not temporally change. In recent years, a compound eye camera and an image pickup device capable of performing distance distribution determination of a phase difference scheme have been developed. A distance distribution and the like of a situation are seen. Therefore, it may be detected that no change in the distance distribution occurs and determined that no or little change of the target object exists. In the body cavity 112, if the relation between the background and the target part 123 can be grasped according to a distribution of intensity of reflection of illumination light and the relation does not greatly change, it may be considered that a target of compensation of a movement is a movement of the user. The movement of the user is solely a rotational movement. Therefore, movement compensation control for assuming a peculiar movement of the user and controlling shift or zoom of the image may be performed according to a wearing part. Such a movement may be specified by a pattern of a movement of a joint related to the wearing part. Although the movement can also be specified by work content or specialty of a device, the movement may be manually inputted in advance.

In step S47, the range switching section 71a determines on the basis of information from the state determining section 72b whether finger bending is started. When determining that the finger bending is not started, the range switching section 71a shifts the processing to step S56 and determines whether zoom is designated. When the zoom is not designated, the range switching section 71a shifts the processing to step S51. When the zoom is designated, in step S57, the range switching section 71a executes zoom processing in an image center to obtain a display image and thereafter shifts the processing to step S51. Note that the display image is displayed on the display section 83 in step S43.

The surgeon moves a position of the finger 100 while confirming the display image displayed on the display section 83 to thereby bring the electric knife 93 of the medical instrument 70 into contact with the target part 123. As shown in FIG. 13, by bending and stretching the finger 100 in an arrow 132a direction, it is possible to incline the electric knife 93 in an arrow 132b direction. The surgeon dissects the target part 123 with the electric knife 93 with operation of bending, stretching, and moving the finger 100. Energy input to the electric knife 93 may be performed by the doctor using a footswitch, performed by the doctor, for example, moving the mouth, or may be operated by another finger or the like. In this way, the doctor performs a lot of treatment requiring concentration. It is important to secure flexibility of various parts of the doctor. A solution by a wearable device not restricted by the device is important. Besides, in the wearable device, it is unnecessary to grip or support the treatment section 73 using a finger other than the finger 100. Flexibility is given to other fingers. Therefore, it is possible to perform other work such as suture and hemostasis with dedicated instruments using the other fingers.

A change in the inclination angle of the second frame 92 by the bending and stretching of the finger 100 is determined by the state determining section 72b. The state determining section 72b outputs acquired information concerning the change in the inclination angle to the range switching section 71a. When determining in step S47 that the bending and stretching of the finger 100 is performed, in step S48, the range switching section 71a changes a direction of the tracking target object according to the finger bending and shifts or zooms the image to generate a display image such that an image portion corresponding to the direction of the tracking target object in the picked-up image by the image acquiring section 72a is located in the screen center. Note that the explanation is based on the premise that the finger bending of the user is a main factor of the phase position change with respect to the target object. Since the dedicated device is as explained above, design may be performed on the basis of the dedicated device. However, a process for such confirmation may be inserted in step S47.

That is, irrespective of the bending and stretching of the finger 100, in a state in which the tracking target object, which is the target part 123, is always located in the screen center of the display section 83, the surgeon can perform dissection work by the electric knife 93 while observing the target part 123 in the display section 83. Consequently, it is easy for the surgeon to confirm the target part 123. The surgeon is capable of treating the target part 123 with simple work of moving the finger 100. The explanation is based on the premise that the movement of the finger of the user is a main factor of the relative position change with respect to the target object. Therefore, the range switching section 71a may first confirm a result obtained by determining in an image given from the image acquiring section that the target object is present in the same position in a background. For example, the range switching section 71a may always confirm, in the image, a positional relation between the target part and the other parts and reflect the positional relation on the branch in step S47. That is, for example, only when the target part is stopped, the range switching section 71a may determine in step S47 that the finger bending is performed. The range switching section 71a does not have to output the finger bending OK signal except in such a situation. The range switching section 71a displays a result of finger bending OK on the eyeglass-type terminal or the like.

In step S49, the range switching section 71a performs blur determination. When determining that blur does not occur in the image, the range switching section 71a shifts the processing to step S54 and determines whether zoom is designated. When the zoom is not designated, the range switching section 71a shifts the processing to step S51. When the zoom is designated, in step S55, the range switching section 71a executes zoom processing in the image center to obtain a display image and thereafter shifts the processing to step S51. The display image is obtained by shifting or zooming the image such that the image portion of the tracking target object is located in the screen center. The display image is displayed on the display section 83 in step S43.

When determining in step S49 that blur occurs, in the next step S50, the range switching section 71a performs image stabilization with image processing and thereafter shifts the processing to step S51.

In step S51, the control section 71 determines whether terminal OFF operation is performed. When the terminal OFF operation is not performed, the control section 71 returns the processing to step S43. When the terminal OFF operation is performed, in step S52, the control section 71 stops the power supply to the respective sections of the medical instrument 70 and transmits a command for turning off the display of the display section 83 to the control section 81 via the communication sections 76 and 86. Consequently, the control section 81 turns off the display of the display section 83.

Note that the flow of FIG. 12 is explained assuming that the tracking target object is present within the image pickup range of the image acquiring section 72a irrespective of the direction and the like of the finger 100. However, depending on a displacement amount of the finger 100, it is also likely that the tracking target object deviates from the image pickup range. Therefore, in this case, the display image is fixed in a state in which the target object in the direction of the tracking target object present in the image pickup range last is located in the screen center. When the tracking target object is present (captured) in the image pickup range again, a display image is generated to locate, in the screen center, an image portion in a position on a picked-up image of the tracking target object in that case.

(Modification)

Incidentally, in the example shown in FIG. 9, the circuit section 89 including the battery 75 is explained as being disposed in the insertion section 90. However, the insertion section 90 is desirably light in weight when operability of the medical instrument 70 is taken into account. In some cases, it is difficult to secure a sufficient capacity of the battery 75. Therefore, a configuration is also conceivable in which the battery 75 and the like are disposed in a portion other than the insertion section 90. It is explained above that, although the eyeglass-type terminal and the treatment instrument (the medical instrument) are worn on separate places, the eyeglass-type terminal and the treatment instrument can be regarded as one device and, if one common control section or the like exists, the common control section can be used as both of the control section 71 and the control section 81. However, power supplies and the like of the eyeglass-type terminal and the treatment instrument may be used in common.

Figure 14:
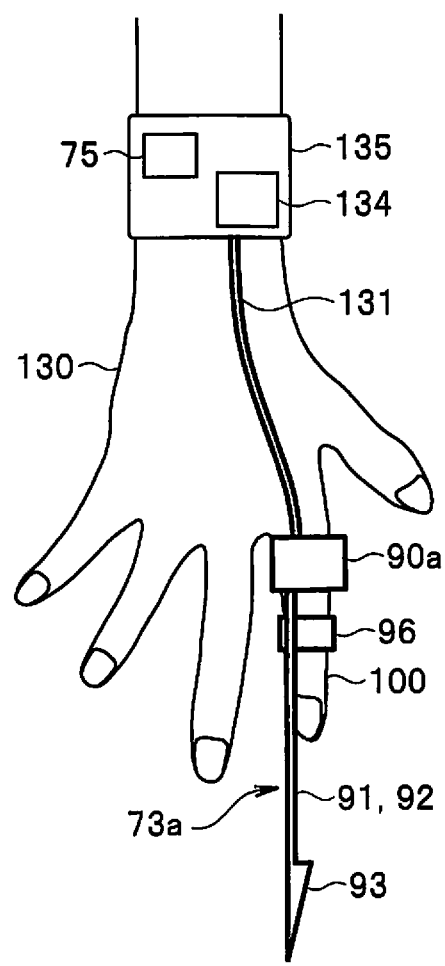
FIG. 14 is an explanatory diagram showing a modification.

FIG. 14 is an explanatory diagram showing such a modification. A treatment section 73*a* is different from the treatment section 73 shown in FIG. 9 in that an insertion section 90*a* not including the circuit section 89 is adopted. A cable 131 including a plurality of wires connected to a plurality of wires inserted through the first frame 91 is connected to the insertion section 90*a*. The cable 131 is wired on a hand 130 of a surgeon. The respective wires on an inside of the cable 131 are connected to a circuit section 134 and the battery 75 mounted on a wristband 135 wound on a wrist of the surgeon. Note that the circuit section 134 includes necessary circuits of the medical instrument 70.

With such a configuration, since the circuit section 134 and the battery 75 having relatively large weights are not mounted on the insertion section 90*a*. Therefore, the surgeon is capable of relatively easily moving the finger 100. Note that, in FIG. 14, an example is shown in which the battery 75 and the circuit section 134 are mounted on the wristband 135. However, a configuration may be adopted in which a light source is disposed on the wristband 135 and light from the light source is transmitted by a light guide and emitted as illumination light.

In this way, in the present embodiment, a tracking target object is set and a change in a direction to the tracking target object is detected to correct a portion of a picked-up image disposed in an image center. Consequently, it is possible to obtain a display image in which the tracking target object is displayed in the screen center. In this way, even when the image acquiring section is displaced according to work, it is possible to perform image pickup that surely grasps the tracking target object.

The present invention is not limited to the embodiments per se. In an implementation stage, the components can be modified and embodied without departing from the spirit of the present invention. Various inventions can be formed by appropriate combinations of a plurality of components disclosed in the embodiments. For example, several components of all the components explained in the embodiments may be deleted.

Note that, even if the operation flows described in the claims, the specification, and the drawings are explained using "first", "next", and the like for convenience, this does not mean that it is essential to implement the operation flows in the order. It goes without saying that portions not affecting the essence of the invention in the respective steps configuring the operation flows can be omitted as appropriate.

Results generated by a large number of branches and the like are simplified and explained herein. However, it goes without saying that more information for making a decision may be used. In recent years, it is known that artificial intelligence, machine learning, deep learning, and the like are effective concerning what kind of control is performed under what kinds of conditions. The device used by the professional explained herein is in a field where it is expected that techniques of authorities, experienced people, and the like in the art are linked to education of the next generation. In the present invention, the respective information acquisition characteristics are improved by making full use of information such as sounds and images. If experts use information indicating when switching of the characteristics is important and accumulate condition data during satisfactory switching, it is possible to construct a more user-friendly system using the condition data as teacher data. The embodiments including such a case are written and explained herein with a most plainly explained method. Therefore, it goes without saying that the present invention is a technique focusing on future developments in the direction. In the technique in which a large number of devices cooperate explained herein, it goes without saying that adaptation and applied design are possible irrespective of where control sections of which devices are present. If it is possible to grasp a relation between the user and the target object or a relation between the background and the target object and these relations do not greatly change, it is possible to specify a target of compensation of a movement. In the respective embodiments explained above, the ways for determining a situation in which a movement of the user is considered to be predominant are enumerated. However, in the determination, various variables such as a situation, a wearing part of the device, and work content are related to one another. Therefore, it goes without saying that control may be switched according to a result of learning by artificial intelligence or the like.

Note that, among the techniques explained above, the controls mainly explained in the flowcharts often can be set by computer programs. The computer programs are sometimes stored in semiconductor recording media or other recording media or recording sections. Recording in the recording media or the recording sections may be performed during product shipment. Distributed recording media may be used. The computer programs downloaded via the Internet may be used. External apparatuses may cooperate according to necessity and substitute for several functions and determinations.

What is claimed is:

1. Apparatus comprising:
a) a wearable image acquisition sensor;
b) a wearable tracking sensor that is associated with the wearable image acquisition sensor such that a motion of the wearable tracking sensor causes a motion of the wearable image acquisition sensor; and
c) a controller configured to (1) determine, using output of the wearable tracking sensor, a relative positional relationship change between the apparatus and a tracking target object included in image data output by the wearable image acquisition sensor, and (2) adjust, using the determined relative positional relationship change, a position of the target tracking object within a display screen.

2. The apparatus of claim 1 wherein the controller is configured to adjust the position of the target tracking object so that it is centered within the display screen.

3. The apparatus of claim 1 wherein the tracking sensor is selected from a group of sensors consisting of (A) an imaging sensor, (B) a pivot angle sensor, (C) an acceleration sensor, (D) a direction sensor, (E) an angular acceleration sensor, (F) a drone providing irradiation and captured reflection of laser light, and (G) a displacement sensor.

4. The apparatus of claim 1 further comprising a user interface configured to accept a user input for setting the tracking target object.

5. The apparatus of claim 1 wherein the apparatus is worn by a first person, the target tracking object is a part of a second person, and the display is viewable by both the first person and the second person.

6. The apparatus of claim 1 wherein the apparatus is worn by a physician, the target tracking object is a body part of a patient, and the display is viewable by both the physician and the patient.

7. The apparatus of claim 6 wherein the controller is configured to display the target tracking object on the display screen even after a field of view of the wearable image acquisition sensor no longer includes the target tracking object, whereby the physician can explain a diagnosis to the patient while viewing the display screen.

8. The apparatus of claim 7 further comprising a microphone for capturing the diagnosis explained by the physician,
wherein the controller is configured to record the diagnosis explained by the physician and captured by the microphone.

9. The apparatus of claim 1 wherein the wearable tracking sensor is mechanically linked with the wearable image acquisition sensor such that the motion of the wearable tracking sensor is mechanically linked with the motion of the wearable image acquisition sensor.

10. The apparatus of claim 1 wherein the wearable tracking sensor and the wearable image acquisition sensor are included in a wearable unit.

11. A method for controlling an apparatus including a wearable tracking sensor and a wearable image acquisition sensor that is associated with the wearable tracking sensor such that a motion of the wearable tracking sensor causes a motion of the wearable image acquisition sensor, the method comprising:
   a) receiving output from the wearable tracking sensor;
   b) determining, using the received output of the wearable tracking sensor, a relative positional relationship change between the apparatus and a tracking target object included in image data output by the wearable image acquisition sensor; and
   c) adjusting, using the determined relative positional relationship change, a position of the target tracking object within a display screen.

12. The method of claim 11 wherein the tracking sensor is an image sensor,
   wherein the wearable information acquisition sensor is a set of microphones, and
   wherein the act of adjusting includes adjusting the information acquisition direction of the set of microphones.

13. The method of claim 11
   wherein the act of adjusting includes centering the position of the target tracking object within the display screen.

14. The method of claim 11 wherein the tracking sensor is selected from a group of sensors consisting of (A) an imaging sensor, (B) a pivot angle sensor, (C) an acceleration sensor, (D) a direction sensor, (E) an angular acceleration sensor, (F) a drone providing irradiation and captured reflection of laser light, and (G) a displacement sensor.

15. The method of claim 11 further comprising:
   accepting a user input for setting the tracking target object.

16. The method of claim 11 wherein the apparatus is worn by a first person, the target tracking object is a part of a second person, and the display is viewable by both the first person and the second person.

17. The method of claim 11 wherein the apparatus is worn by a physician, the target tracking object is a body part of a patient, and the display is viewable by both the physician and the patient.

18. The method of claim 17 wherein the controller is configured to display the target tracking object on the display screen even after a field of view of the wearable image acquisition sensor no longer includes the target tracking object, whereby the physician can explain a diagnosis to the patient while viewing the display screen.

19. The method of claim 18 wherein the apparatus further includes a microphone for capturing the diagnosis explained by the physician, the method further recording the diagnosis explained by the physician and captured by the microphone.

20. A non-transitory computer-readable medium storing processor executable instructions which, when executed by a least one processor, cause the at least one processor to perform a method for controlling an apparatus including a wearable tracking sensor and a wearable image acquisition sensor that is associated with the wearable tracking sensor such that a motion of the wearable tracking sensor causes a motion of the wearable image acquisition sensor, the method comprising:
   a) receiving output from the wearable tracking sensor;
   b) determining, using the received output of the wearable tracking sensor, a relative positional relationship change between the apparatus and a tracking target object included in image data output by the wearable image acquisition sensor; and
   c) adjusting, using the determined relative positional relationship change, a position of the target tracking object within a display screen.

\* \* \* \* \*